(12) United States Patent
Dimitrov et al.

(10) Patent No.: US 9,910,001 B2
(45) Date of Patent: Mar. 6, 2018

(54) FRAGMENT DETECTION METHOD AND APPARATUS

(71) Applicants: Nikola Dimitrov, Tecumseh (CA); Mark John Worsley, Windsor (CA); Ahmad Shawky, Windsor (CA)

(72) Inventors: Nikola Dimitrov, Tecumseh (CA); Mark John Worsley, Windsor (CA); Ahmad Shawky, Windsor (CA)

(73) Assignee: Radix Inc., Maidstone (CA)

(*) Notice: Subject to any disclaimer, the term of this patent is extended or adjusted under 35 U.S.C. 154(b) by 0 days.

(21) Appl. No.: 14/872,489

(22) Filed: Oct. 1, 2015

(65) Prior Publication Data

US 2017/0097312 A1 Apr. 6, 2017

(51) Int. Cl.
*G01J 5/02* (2006.01)
*G01N 25/72* (2006.01)

(52) U.S. Cl.
CPC .............. *G01N 25/72* (2013.01); *G01J 5/025* (2013.01)

(58) Field of Classification Search
CPC .... G01N 25/72; G01N 29/348; G01N 29/228; G01N 21/71; G01N 29/346
See application file for complete search history.

(56) References Cited

U.S. PATENT DOCUMENTS

| | | | |
|---|---|---|---|
| 4,253,766 A * | 3/1981 | Funk | G01N 21/314 250/339.03 |
| 4,764,668 A | 8/1988 | Hayard | |
| 5,229,931 A | 7/1993 | Takeshima et al. | |
| 5,521,843 A | 5/1996 | Hashima et al. | |
| 5,535,522 A | 7/1996 | Jackson | |
| 5,816,096 A | 10/1998 | Ng et al. | |
| 6,497,134 B1 | 12/2002 | Faul et al. | |
| 2001/0036245 A1 | 11/2001 | Kienzle et al. | |
| 2002/0038159 A1 | 3/2002 | Gass | |
| 2002/0191814 A1 | 12/2002 | Ellis et al. | |

(Continued)

OTHER PUBLICATIONS

Tsai, A Versatile Camera Calibration Technique for High-Accuracy 3D Machine Vision Metrology Using Off-the-Shelf TV Cameras and Lenses, IEEE Journal of Robotics and Automation, vol. RA-3, No. 4, Aug. 1987.

*Primary Examiner* — David Porta
*Assistant Examiner* — Mamadou Faye
(74) *Attorney, Agent, or Firm* — Young Basile Hanlon & MacFarlane, P.C.

(57) ABSTRACT

A method and apparatus for detecting machined substrate fragments by thermography. A heat source applies heat to a surface of machined component, the surface providing access to one or more internal chambers within an interior space of the component. The application of heat is sufficient in temperature and duration to cause a fragment temperature elevation rate in at least one machined substrate fragment present in at least one internal chamber that is greater than temperature elevation rate of the component. An IR detection device operably connected to a visual output device captures the IR signal from the component surface following the application of heat and outputs a thermal image of the component. Heat elevation points within the thermal image correspond with the presence of machined substrate fragments within at least one internal chamber of the component.

30 Claims, 22 Drawing Sheets

(56) References Cited

U.S. PATENT DOCUMENTS

| | | | |
|---|---|---|---|
| 2005/0008215 A1* | 1/2005 | Shepard | G01N 25/72 |
| | | | 382/141 |
| 2005/0111726 A1 | 5/2005 | Hackney et al. | |
| 2005/0123188 A1 | 6/2005 | Leikas et al. | |
| 2005/0201610 A1 | 9/2005 | Hertzman et al. | |
| 2006/0238741 A1* | 10/2006 | Ninomiya | F23N 5/24 |
| | | | 356/5.01 |
| 2007/0188606 A1 | 8/2007 | Atkinson et al. | |
| 2007/0217672 A1* | 9/2007 | Shannon | G06T 7/0006 |
| | | | 382/152 |
| 2010/0074515 A1* | 3/2010 | Zhao | G01N 25/72 |
| | | | 382/149 |
| 2011/0248168 A1* | 10/2011 | Eren | G01B 11/2522 |
| | | | 250/339.11 |
| 2011/0249700 A1* | 10/2011 | Nakagawa | G01N 25/72 |
| | | | 374/4 |
| 2013/0160552 A1* | 6/2013 | Nakata | G01N 29/2418 |
| | | | 73/628 |
| 2013/0203043 A1* | 8/2013 | Ozcan | G06F 19/3487 |
| | | | 435/5 |
| 2013/0334753 A1* | 12/2013 | Stanifer | B23Q 3/069 |
| | | | 269/32 |
| 2014/0257569 A1* | 9/2014 | Yip | G05B 15/02 |
| | | | 700/275 |
| 2015/0300882 A1* | 10/2015 | Falk | G01R 31/311 |
| | | | 324/754.21 |

* cited by examiner

FRAGMENT DETECTION METHOD AND APPARATUS

BACKGROUND

Disclosed is a method and apparatus for detecting machined substrate fragments within one or more internal chambers of a machined metal component, and more particularly, the use of non-destructive thermography for the detection of machined substrate fragments.

Non-destructive thermography for defect detection is generally known in the art. U.S. Pat. No. 4,996,426 discloses an apparatus for subsurface flaw detection of a continuously moving working piece, specifically, a rolled, worked metallic sheet. Heat is applied to a bottom surface of the workpiece causing thermal flow from the bottom to a top surface. Low thermal conductivity defects within the workpiece, including foreign material inclusions and subsurface cracks, cause thermal lines to flow around the defect creating low temperature areas on the top surface. An IR-detection device captures a thermal image of the top surface, wherein low temperature areas on the thermal image correlate with subsurface defects within the workpiece.

U.S. Pat. No. 8,581,975 and U.S. Pat. No. 5,834,661 disclose the detection of subsurface defects using thermography. U.S. Pat. No. 8,581,975 discloses a method and apparatus in which an induction coil applies heat to a powder-metallic component to cause a thermal increase flow through the body of the component and heat the component substantially uniformly throughout the component body. An IR-detection device creates a thermal image of the component following induction heating and subsurface inclusions, such as foreign metallic compounds, appear as different colors within the thermal image. U.S. Pat. No. 5,834,661 discloses a method wherein one side of a component is placed near a thermoplate and an opposing side is placed near a vacuum. As heat flows from the heated side to the vacuum side as the component cools, an IR-detection device captures a transient thermal image of the component. Subsurface inclusions appear as temperature/color variations within the transient thermal image.

Similarly, U.S. 2013/0261989 and U.S. Pat. No. 5,654,977 disclose methods of detecting subsurface defects at varying depths, such as foreign metal inclusions and subsurface laminations, using transient thermal imaging techniques.

The referenced apparatuses and methods detect defects such as foreign material and subsurface defects. Many of these disclosed apparatuses and methods detect subsurface defects. However, these disclosed methods and apparatuses, as well as others that are well known in the art, rely on a difference in material substance between the defect and the component substrate in order in order to effectively locate such defects using thermography techniques. In typical machining applications, machined substrate fragments, which fragments are composed of the same material substance as the component itself, are removed from the machined component body. These substrate fragments may be resident in one or more internal chambers of a machined component following a machining operation, which, if left undetected, can create component malfunctions following the installation and/or use of the machined component. It is an object of the disclosed method and apparatus to overcome these shortcomings in the art.

BRIEF SUMMARY

A method of inspecting a machined metal component, the machined metal component defining a component body including an outer surface, and an interior region having at least one internal chamber, for detecting machined substrate fragments resident in the at least one internal chamber is herein described. The at least one internal chamber communicates with at least one aperture defined in the outer surface providing open exposure of the at least one internal chamber to the ambient surrounding environment. The method may include on or more of the following steps: applying heat to at least a section of the outer surface of the machined metal component outer surface of a provided machined metal part with the application of heat is sufficient in temperature and duration to cause a fragment temperature elevation in at least one machined substrate fragment present in at least one internal chamber defined in the machined metal component as well as a component temperature elevation in the machined metal component with the fragment temperature elevation having a fragment temperature elevation rate and the component temperature elevation having a component temperature elevation rate such that the fragment temperature rate is greater than the component temperature elevation rate. The process also includes a step of producing a thermal image of temperature distribution of the outer surface of the machined metal component following the application of heat as well as a step of detecting one or more heat elevation points within the thermal image of the temperature distribution of the outer surface; the heat elevation points indicating the presence of at least one machined substrate fragment within one or more internal chambers of the machined metal component.

In some embodiments, the profile may be an open cross-sectional profile of the machined metal component.

The heating step may include applying at least one pulse of hot air delivered to the outer surface, and in some embodiments, the heating step may include applying heat consecutively to a group of locations defined on the outer surface for a predetermined amount of time. Heat may be applied to each of the group of locations defined on the outer surface sequentially following the expiration of the predetermined amount of time at each location.

In some embodiments, the thermal image of temperature distribution is a real-time transient image.

An apparatus for inspecting a machined metal component following a machining operation is herein disclosed. The machined metal component includes a component body having at least one internal chamber. The apparatus herein disclosed includes a. means for applying heat to at least a section of an outer surface of the machined metal component to be investigated; means for moving the heating means to various locations relative to the outer surface. The device can also include a controller mechanism that can be operably connected to the positioning means and/or the heating means to permit selective control of the application of heat to the outer surface of the machined metal part under investigation and the positioning of the heating means relative to the outer surface. The device also includes a thermal detection device such as an infrared (IR) detection device that is positioned to detect an IR radiation signal emitted from the section of the outer surface under investigation. A signal processor can be operably connected to the IR detection device to receive and process the detected IR radiation signal and provide data to a suitable output device. Where desired or required, the device and include visual output member operatively connected to the signal processor for receiving the processed IR radiation signal and displaying a thermal image of the IR radiation signal emitted from the section of the outer surface.

In some embodiments, the apparatus may further include a housing having an outer wall defining an inner chamber, the inner chamber containing the IR detection device, the positioning means and the heating means. The housing may include a drawer configured to receive and retain the machined metal component, the drawer being configured for movement from an outer loading position wherein at least a portion of the drawer is outside of the inner chamber to allow loading of the machined metal component, and an inner inspection position wherein the drawer is inside of the inner chamber. In some embodiments, the drawer may include locking means for selectively locking and unlocking the drawer within the inner chamber when the drawer is in the inner inspection position. The apparatus may further include a sensor mechanism, the sensor mechanism detecting when the drawer is in the inner inspection position, the sensor operably connected to the controller mechanism to permit activation of the heating means and positioning means when the drawer is in the inner inspection position.

In some embodiments, the positioning means may move the heating means within a single plane located at a predetermined height relative to the outer surface.

In some embodiments, the positioning means may include one or more servo-actuated linear sliders and the heating means may be mounted to the one or more servo-actuated linear sliders for movement. In some embodiments, the one or more servo-actuated linear sliders may include an X-axis linear slider for moving the heating means within an X-axis within a single plane and a Y-axis linear slider for moving the heating means within a Y-axis within a single plane.

In some embodiments, the apparatus may further include a component movement mechanism, the component movement mechanism allowing for selective displacement of the machined metal component relative to the heating means to allow for heating of various sections of the machined component. The component movement mechanism may comprise a rotational mechanism, the rotational mechanism rotating the machined metal component relative to the heating means. In some embodiments, the rotational mechanism may comprise one or more pneumatic cylinders, the pneumatic cylinders may be releasably securable to the machined metal component.

In some embodiments, the controller mechanism may include a programmable logic controller.

In some embodiments, the heating means may include a heat gun.

In some embodiments, the IR detection device may include an IR camera.

In some embodiments, the signal processor may include a computer.

BRIEF DESCRIPTION OF THE SEVERAL
VIEWS OF THE DRAWINGS

To easily identify the discussion of any particular element or act, the most significant digit or digits in a reference number refer to the figure number in which that element is first introduced.

DETAILED DESCRIPTION

Figure 1:
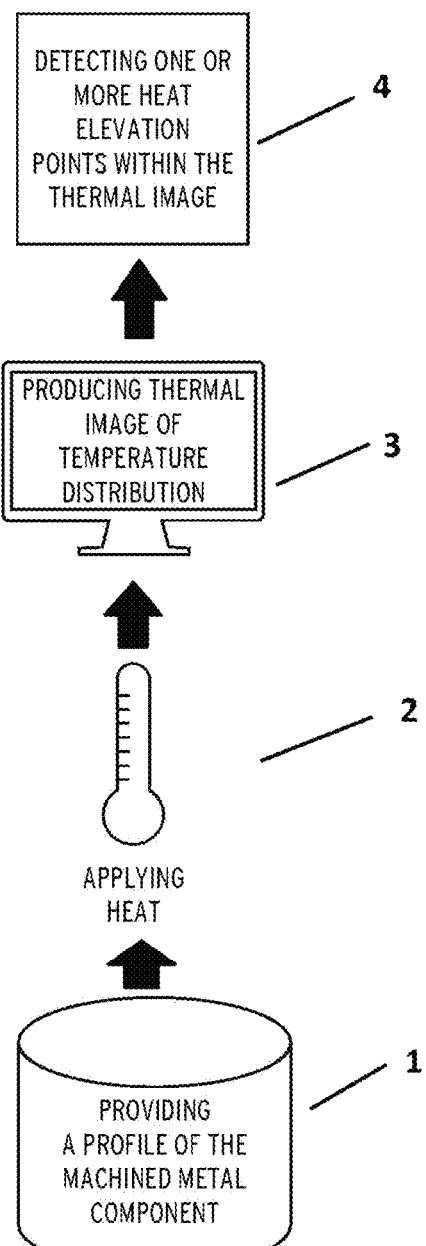
FIG. 1 illustrates a routine for detecting machined substrate fragments resident in the at least one internal chamber in accordance with one embodiment.
Figure 2:
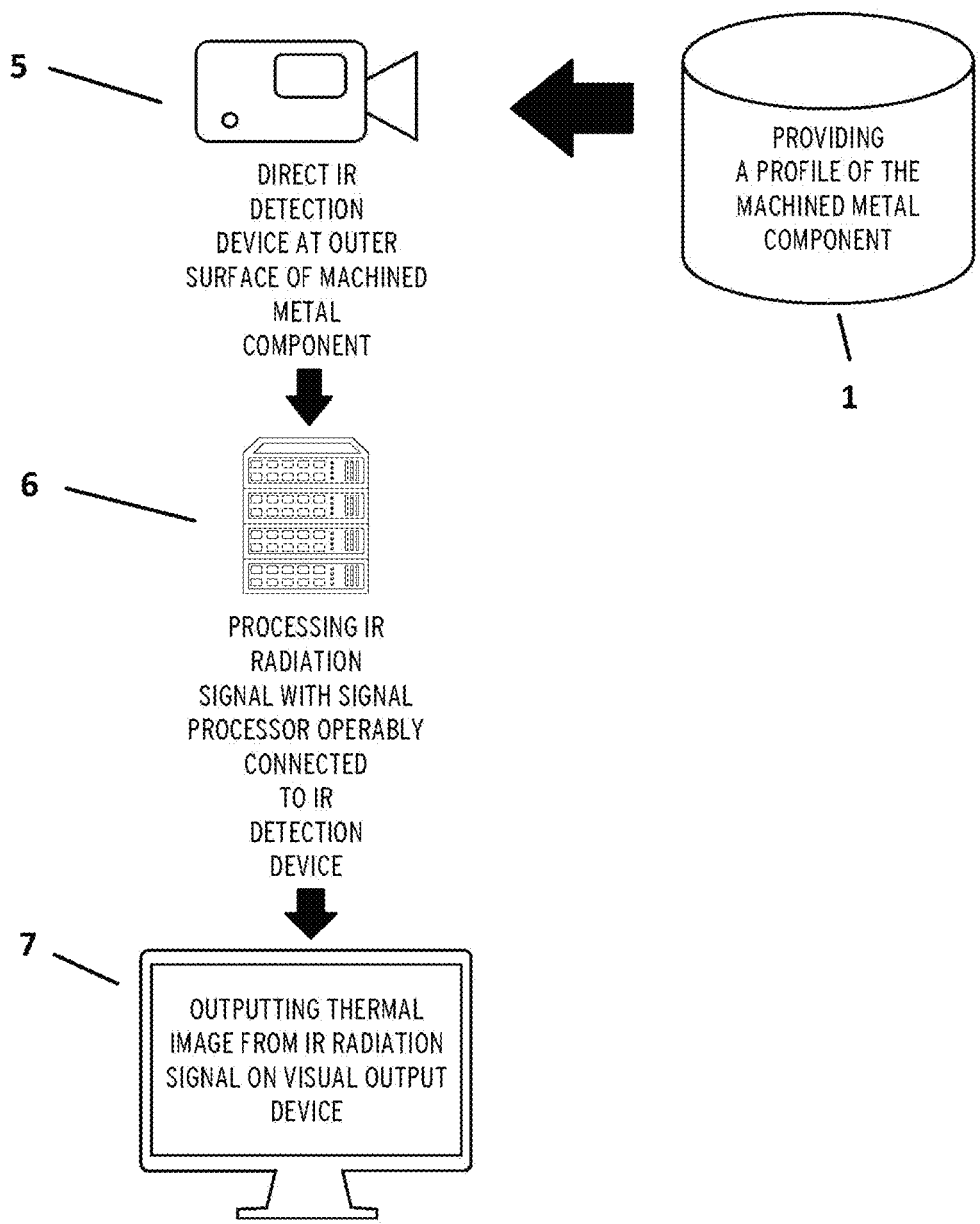
FIG. 2 illustrates a routine for detecting machined substrate fragments resident in the at least one internal chamber in accordance with one embodiment.

The process as disclosed herein is predicated on the unexpected discovery that transient thermal changes applied to a machined metal component can be employed to detect and locate machining debris lodged in interior channels defined on the machined metal component. The process as disclosed herein has particular efficacy when used to detect machining debris that is composed of metal material derived from the machine metal component; i.e. metal fines and the like.

In some embodiments, the thermal image is produced as the temperature of the outer surface and the at least one machined substrate fragment begins cooling to the temperature of the ambient surrounding environment following the heating step.

In some embodiments, producing the thermal image may include directing an IR detection device at the outer surface of the machined metal component to detect an IR radiation signal emitted from the outer surface, processing the IR radiation signal with a signal processor operably connected to the IR detection device and producing and outputting the thermal image from the IR radiation signal on a visual output device operatively connected to the signal processor. Processing the IR radiation signal with a signal processor may further include formatting the signal with a low-pass size filter to remove heat elevation points smaller than a predetermined minimum size from the thermal image. Processing the IR radiation signal with a signal processor may further include formatting the signal with a high-pass size filter to remove heat elevation points larger than a predetermined maximum size from the thermal image.

In some embodiments, the disclosed method may further include calculating at least one temperature difference value between the temperature of the at least one heat elevation points and the component temperature elevation. Processing the IR radiation signal with a signal processor may further include formatting the signal with a low-pass temperature filter to remove heat elevation points corresponding with the temperature difference value being smaller than a predetermined minimum temperature difference value from the thermal image. In some embodiments, processing the IR radiation signal with a signal processor may further include formatting the signal with a high-pass temperature filter to remove heat elevation points corresponding with the temperature difference value being larger than a predetermined maximum temperature difference value from the thermal image.

In some embodiments, the IR detection device may include an IR camera.

In some embodiments, the signal processor may be a computer and the output device may be a computer screen operably connected to the computer. The computer may be configured to process the IR radiation signal and output the IR radiation signal in the form of a color-temperature map thermal image on the computer screen. In some embodiments, the color-temperature map thermal image may be configured to display colors corresponding with pre-defined temperatures across the thermal image of the outer surface of the machined metal component.

In some embodiments, the heat elevation points appear as a different color from surrounding areas of the outer surface within the color-temperature map thermal image.

In some embodiments, the machined metal component may include a metal or a metallic alloy.

The machined substrate fragment may be substantially surrounded by ambient air within the internal chamber. The machined substrate fragment may constitute a metallic chip separated from the machined component body during the machining process.

Figure 3:
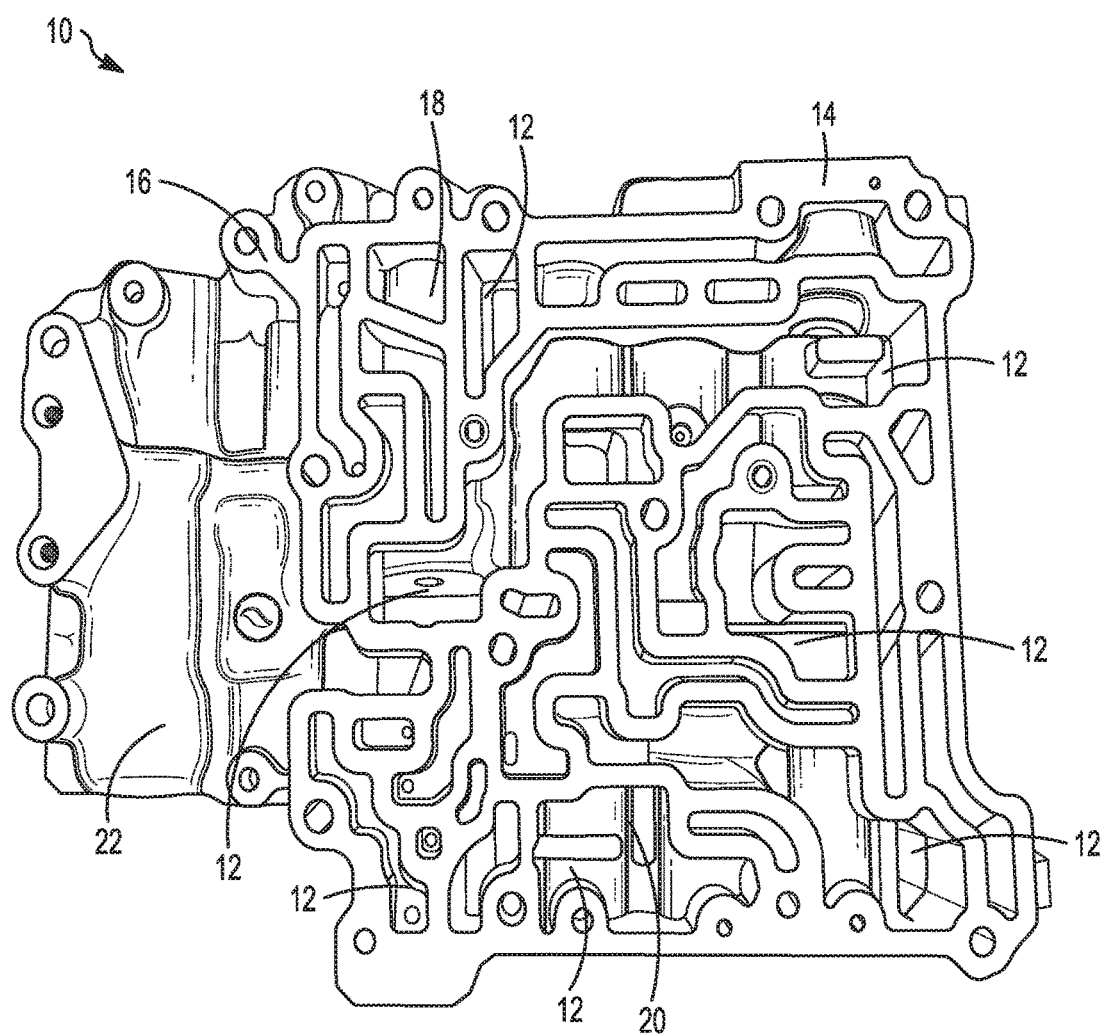
FIG. 3 is a picture of a sample machined metal component to be inspected in accordance with one embodiment.

In some embodiments, the heat elevation points may include a positive temperature gradient between the heat elevation points and the surrounding outer surface, the positive temperature gradient corresponding with the presence of a machined substrate fragment In the process disclosed herein, the target machined metal component inspection method as disclosed herein includes the step of providing a profile the machined metal component as in reference numeral 1 in FIG. 1. The machined metal component is typically one which is prepared for subsequent processing and/or assembly. Suitable metal parts will be configured to include a component body having at least one internal chamber defined therein. The at least one internal chamber can be defined in the component body by any suitable method including, but not limited to, casting, machining and the like. In the method disclosed the machined metal component may be a component part of a final mechanical part or mechanism that can be assembled in later subsequent post inspection steps to produce a final assembled component. The machined metal component can be a profile or other suitable sub-device. In certain applications, the profile can be an open cross-sectional profile across the machined metal component. The machined metal component under inspection by the process disclosed can have at least one internal chamber that communicated with at least one aperture defined in the outer surface of the machined metal component thereby providing open exposure of the at least one internal chamber to the ambient surrounding environment. One non-limiting example is depicted in FIG. 3 and is discussed in greater detail subsequently.

The method also includes a step of applying heat 2 to a least a section of the outer surface of the machined metal part component under inspection. The application step 2 proceeds for an interval and at a temperature sufficient to cause a fragment temperature elevation in at least one machined substrate fragment present in the at least one internal chamber. The heat application step 2 also causes a component temperature elevation in the machined metal component. The heat application step 2 provides a fragment temperature elevation having a fragment temperature elevation value and a component temperature elevation having a component temperature elevation value in which the fragment temperature elevation value is greater than the component temperature elevation value. Following the application step 2, the method also includes the steps of producing a thermal image of temperature distribution 3 and detecting one or more heat elevation points within the thermal image 4. As the fragment temperature elevation value is greater than the component temperature elevation value, the heat elevation points indicate the presence of at least one machined substrate fragment within one or more internal chambers of the machined metal component.

Producing a thermal image 3 may include the steps of directing an IR detection device at the outer surface of the machined metal component 5, processing the IR radiation signal captured by the IR detection device with a signal processor operably connected to the IR detection device 6, and outputting a thermal image from the IR radiation signal on a visual output device 7. The method also includes a step in which the difference between the fragment temperature elevation value and the component temperature elevation value is detected and located relative to the machined metal component. In certain embodiments of the process disclosed, the detection and location is accomplished by the production of a thermal image of temperature distribution of the outer surface of the machined metal component. The producing step 3 occurs after the heat application step 2.

Once the differences in fragment temperature elevation values and machined metal component have been ascertained, the method includes detecting one or more heat elevation points within the thermal image of the temperature distribution of the outer surface of the machined metal component as at reference numeral 8. The elevation points are indicative of the presence of at least one machined substrate fragment present within one or more internal chambers of the machined metal component. Where desired, the temperature elevation points can be detected with a suitable infrared detection device.

As seen in the exemplary embodiment of FIG. 3, the machined metal component 10 comprises standard transmission component valve body, which valve body would be implemented for use in high performance engine transmissions. The machined metal component 10 of the exemplary embodiment is cast from cast iron. This valve body of the exemplary embodiment controls the shifting process in automatic transmissions. The valve body of the exemplary embodiment contains a one or more internal chambers 12, through which an automotive hydraulic system would push pressurized hydraulic fluid in order to activate and deactivate appropriate clutches and band servos to control up and down shifting of gears. As such, it is important that such internal chambers 12 remain clear from debris, including substrate debris post-machining, in order to ensure smooth and effective transfer of hydraulic fluid through the internal chambers 12. Presence of substrate fragments within the internal chambers 12 can cause sub-optimal performance and in worst cases scenario transmission failure.

The profile 20 of the exemplary embodiment of FIG. 3 is an open cross-sectional profile having a number of open apertures 18 defined on the outer surface 14. The one or more internal chambers 12 communicate with one or more apertures 18 defined in the outer surface 14 providing open exposure to the interior region 16 of the machined component body 22 and open exposure of one or more internal chambers 12 to the ambient surrounding environment. In the exemplary embodiment illustrated in FIG. 3, one or more internal chambers 12 comprise gear valves of varying shapes and depths within the interior region 16 of the machined metal component 10.

Figure 4:
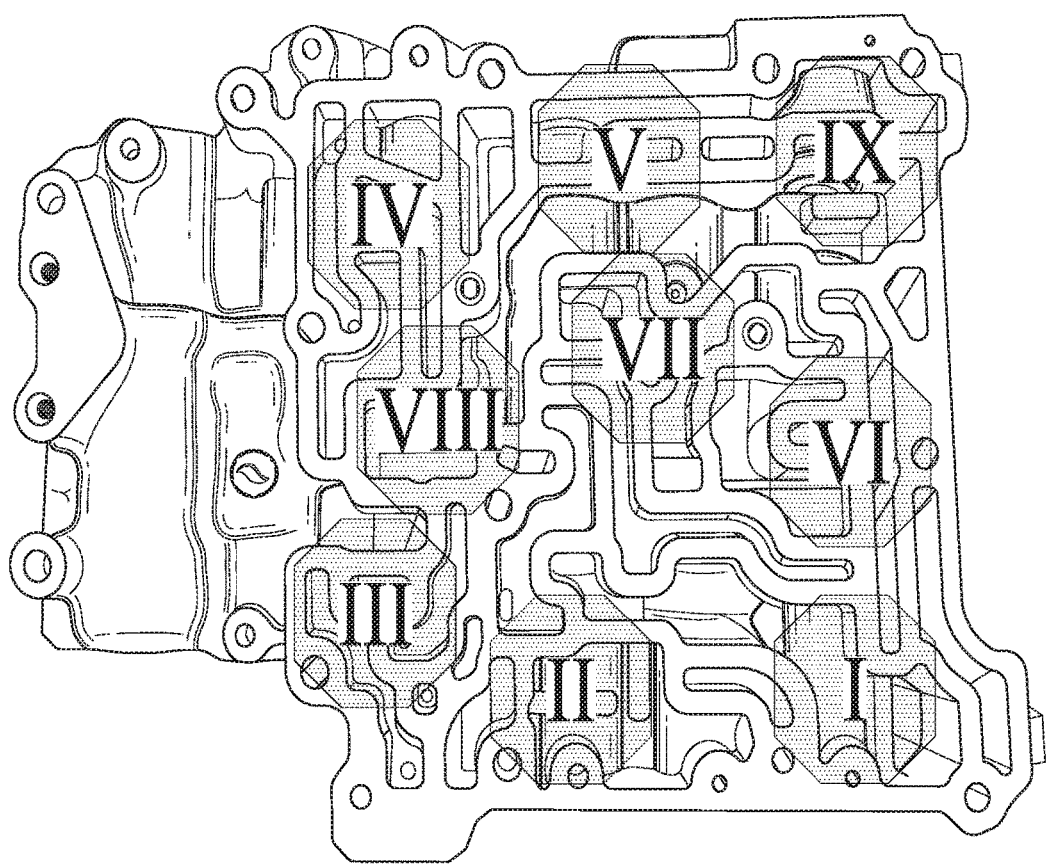
FIG. 4 is a picture of a sample machined metal component with various locations identified on an open cross-sectional profile to be inspected in accordance with one embodiment.

As seen in the embodiment of FIG. 4, the heating step 2 may comprise the step of applying heat either simultaneously or consecutively in a predetermined sequence to a plurality of locations defined on the outer surface 14 of the machined metal component 10. The heating means 70 may apply heat for a predetermined amount of time to each of the plurality of locations. Heat can be applied to each of the locations defined on the outer surface 14 for a suitable defined interval. The heat application interval associated with each location can be the same or can be varied depending on factors such as localized mass, the specific architecture details present in the location, etc. Where sequential heating is employed, it is contemplated that heating at a specific location will commence after the expiration of the predetermined amount of time at the prior location. It is also contemplated that the heating step can occur in a combination of sequential positions.

Referring to the exemplary embodiment of FIG. 4, heat may be applied sequentially to each of the positions I-IX for the following predetermined amount of time at each position:

I—3 seconds
II—5 seconds
III—3 seconds
IV—3 seconds
V—4 seconds
VI—3 seconds
VII—3 seconds
VIII—3 seconds
IX—2 seconds Heating interval variation can be determined based on depth and intricacy of the one or more internal chambers 12 at each position. It is also contemplated that the heating interval can be varied based on details such as potential size of machined substrate fragment 24 to be detected for any specific application. In some applications, particularly small machined substrate fragments 24 may be lodged deeply within intricate chambers, and accordingly, the application of heat must be sustained for longer duration in order to create a sufficient fragment temperature elevation to ensure that the machined substrate fragment will create a heat elevation point in the thermal image following heating.

Referring to the exemplary embodiment of FIG. 4, specifications for this exemplary embodiment require detection of any machined substrate fragment having minimum size of 2 millimeter×2 millimeter surface area. Accordingly, the specific parameters of the heat application step of the method disclosed herein have been calibrated with the above referenced time durations at each position I-IX, the details of which will be discussed below. Given the depth and intricacy of the one or more internal chambers 12 at each location I-IX, and the minimum size requirements for detection of machined substrate fragments, these predetermined time values at each location I-IX ensure that adequate heat has been applied to induce sufficient fragment temperature elevation for any machined substrate fragments positioned within any of the one or more internal chambers 12 at each position. The duration of the application of heat interval per specific position based on fragment detection specification can be deduced by the skilled artisan based upon the teachings contained with in this disclosure. Similarly, specific heating intervals associated with specific locations in the machined metal component can be deduced by the skilled artisan based upon the present disclosure.

Figure 5:
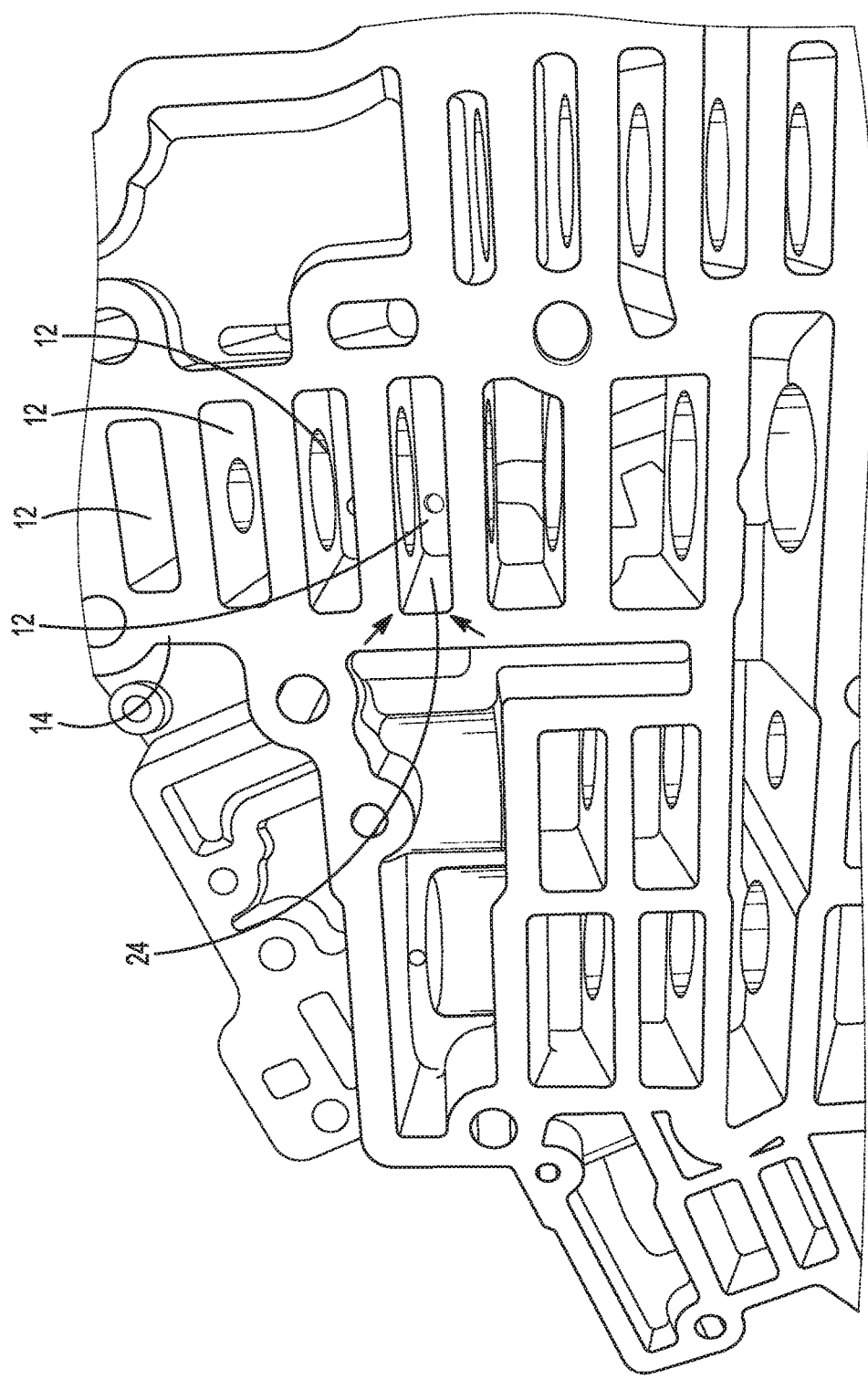
FIG. 5 is a picture of a sample machined metal component with a machined substrate fragment residing in an internal chamber to be inspected in accordance with one embodiment.
Figure 6:
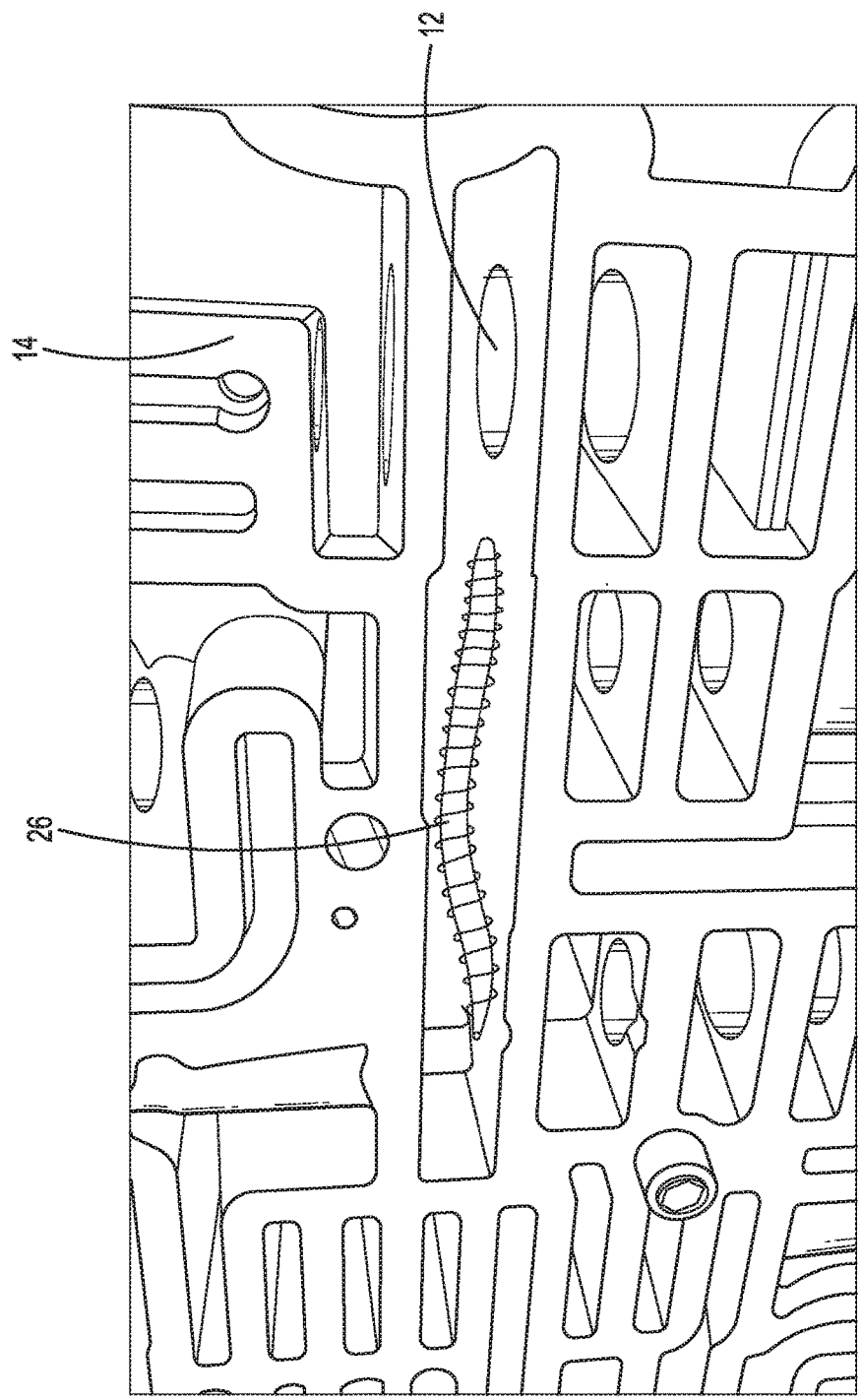
FIG. 6 is a picture of a sample machined metal component with a machined substrate fragment residing in an internal chamber to be inspected in accordance with one embodiment.

As seen in FIG. 5 and FIG. 6, the machined substrate fragment may comprise any substrate fragment that is substantially surrounded by ambient air within the one or more internal chambers 12. FIG. 6 illustrates a machined substrate fragment comprising a metallic chip 26 resident within one or more internal chambers 12. Following machining of the machined metal component 10, such metallic chip 26 separated from the machined component body 22 during the machining process and may become lodged within one or more internal chambers 12 of the machined component body 22. Such metallic chips can cause significant damage if left undetected and the machined metal component 10 is installed in the final product (in this exemplary embodiment, the final product being an automobile).

However, as seen in the embodiment of FIG. 5, the machined substrate fragment may comprise any substrate fragment that is substantially surrounded by ambient air within the one or more internal chambers 12. The machined substrate fragment 24 illustrated in FIG. 5 is attached to and extends outward from the machined component body 22 within the one or more internal chambers 12. As discussed in detail below, based on optimization of the application of heat by the heating means 70, in order to apply heat sufficient in temperature and duration to cause a greater fragment temperature elevation rate than the component temperature elevation rate, as well as the sensitivity of the IR detection device 66 and the signal processor 54, the disclosed method can detect machined substrate fragments of various sizes and shapes. A skilled artisan applying the teachings disclosed herein could detect machined substrate fragments of any shape or size by optimizing resolution as well as the field of view of the IR detection device 66. For example, the IR detection device 66 can be focused on a much smaller area, thereby creating a thermal image with far greater resolution (pixels per millimeter) thereby permitting detection of machined substrate fragments 24 of far smaller sizes.

Figure 7:
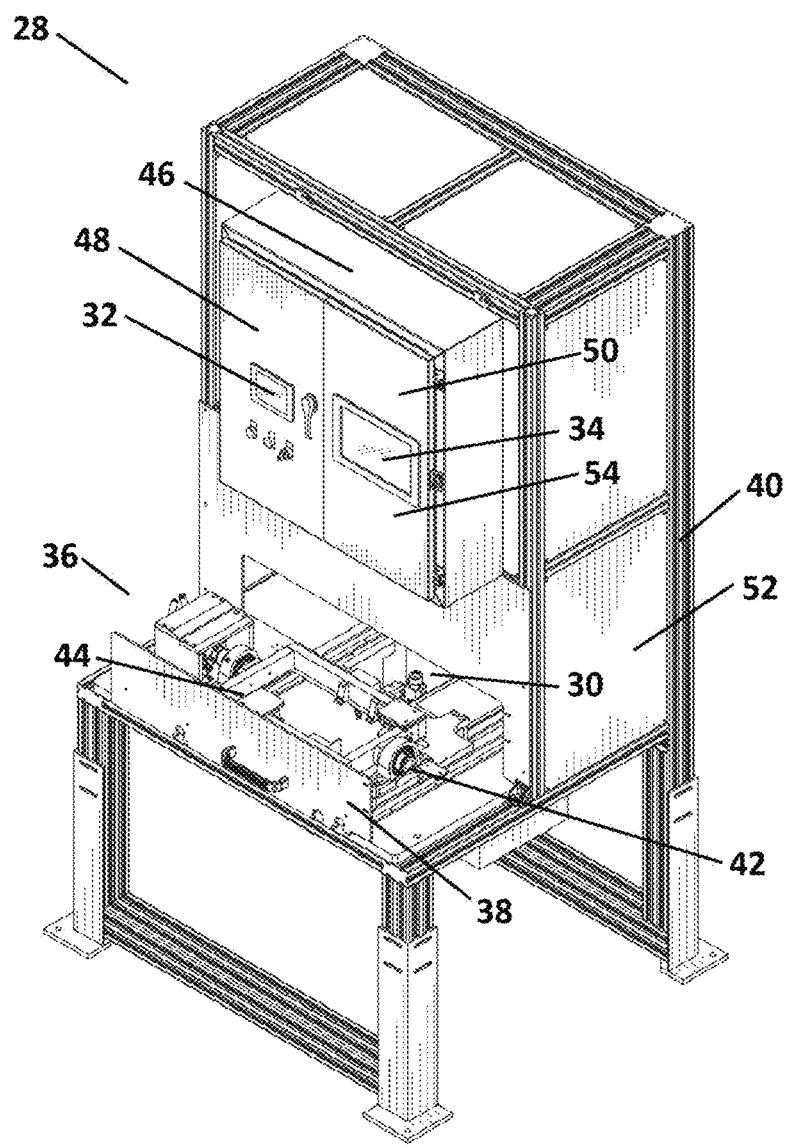
FIG. 7 illustrates a perspective view of the inspection apparatus in accordance with one embodiment.
Figure 8:
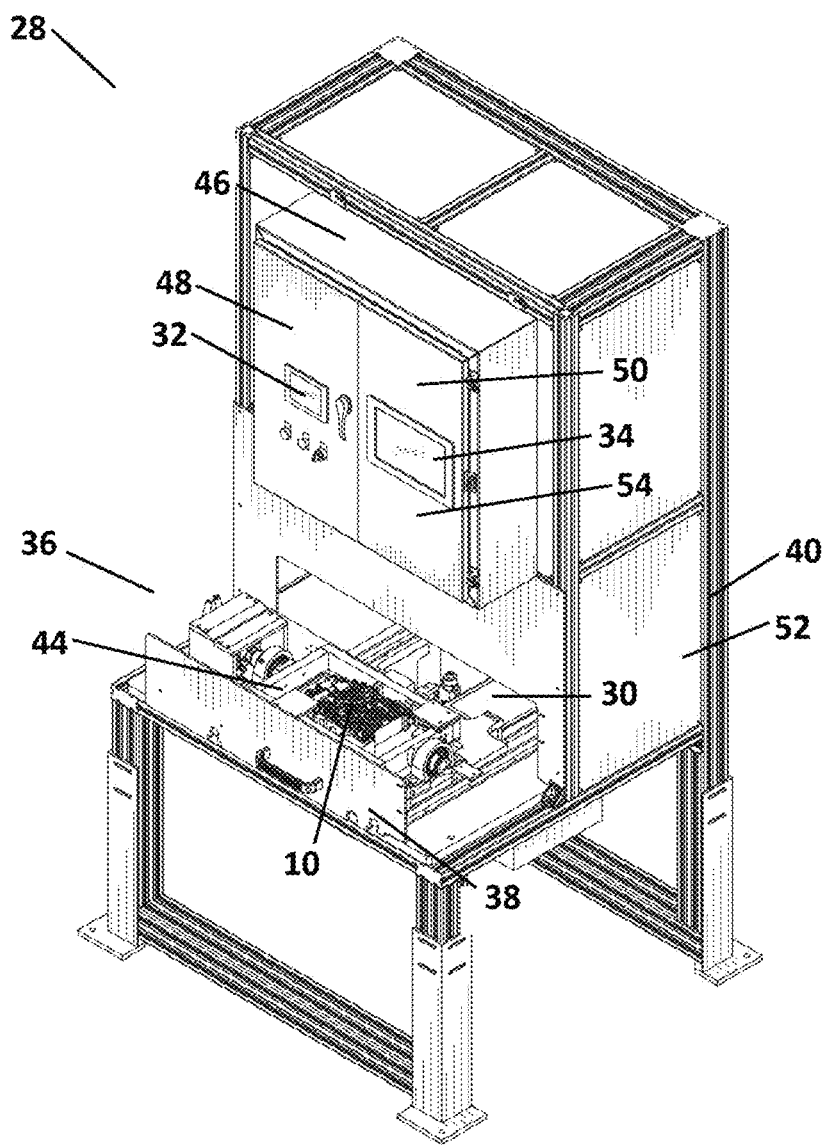
FIG. 8 illustrates a perspective view of the inspection apparatus with a machined metal component loaded for inspection in accordance with one embodiment.

Referring to the embodiment of FIG. 7 and FIG. 8, the apparatus 28 of the exemplary embodiment may comprise a housing 40 having an outer wall 52 defining an inner chamber 30. The apparatus 28 may further comprise a drawer 38, the drawer 38 being configured to receive and retain the machined metal component 10. FIG. 8 illustrates the drawer 38 in the outer loading position 36, wherein at least a portion of the drawer 38 is outside of the inner chamber 30. The outer loading position 36 allows for loading of the machined metal component 10 into the drawer 38 for inspection. Loading can either be manually completed by a user, or automated using automated means, such as a loading robot.

The drawer 38 may also comprise a drawer frame 44. Referring to FIG. 7 and FIG. 8, the drawer frame 44 receives and retains the machined metal component 10. As seen in FIG. 7 and FIG. 8, the machined metal component 10 is loaded into the drawer frame 44 of the drawer 38 in order to secure the machined metal component 10 for inspection.

Figure 11:
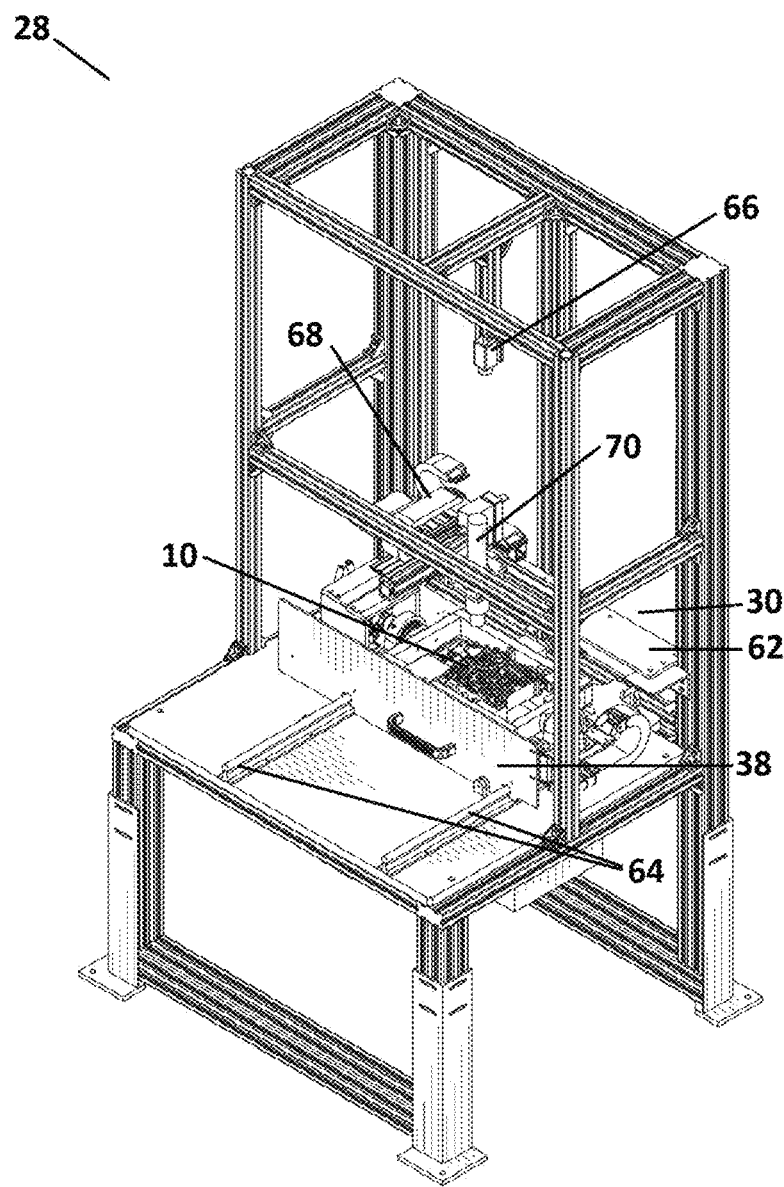
FIG. 11 illustrates a perspective view of the inspection apparatus with outer wall removed and the apparatus in the inner inspection position in accordance with one embodiment.

The apparatus 28 comprises a controller mechanism 32 operably connected to the positioning means 68 and the heating means 70 (illustrated in FIG. 11). The apparatus 28 may also comprise a signal processor 54, the signal processor 54 operably connected to the IR detection device 66 (illustrated in FIG. 11) to receive and process a detected IR radiation signal from the machined metal component 10.

In the embodiment of FIG. 7 to FIG. 10, the controller mechanism 32 and the signal processor 54 may be housed within a control shelf 46, the control shelf having a left shelf door 48 and a right shelf door 50 opening up to an enclosed shelf space (not illustrated) within the control shelf 46.

The controller mechanism 32 may comprise a standard programmable logic controller, such as a standard Allen Bradley programmable logic controller. A person skilled in the art would appreciate that any similar control apparatus that could serve the same function would be an adequate controller mechanism 32. As discussed in detail below, the signal processor 54 may comprise a standard computer equipped with commercially available thermal image processing software. Both the programmable logic controller and the computer of the embodiment of FIG. 7 to FIG. 10 could be housed within the control shelf 46, which control shelf 46 could be attached to the outer wall 52 of the housing 40.

The apparatus 28 may further comprise a visual output device 34, the visual output device 34 being operatively connected to the signal processor 54 for receiving the processed IR radiation signal and displaying a thermal image of the IR radiation signal emitted from the section of the outer surface 14. In the exemplary embodiment of FIG. 7 to FIG. 10, the visual output device 34 may comprise a standard computer monitor screen connected to the signal processor 54 computer housed within the control shelf 46, and as illustrated in FIG. 7 and FIG. 8, may be disposed upon the left shelf door 48 of the control shelf 46.

Figure 9:
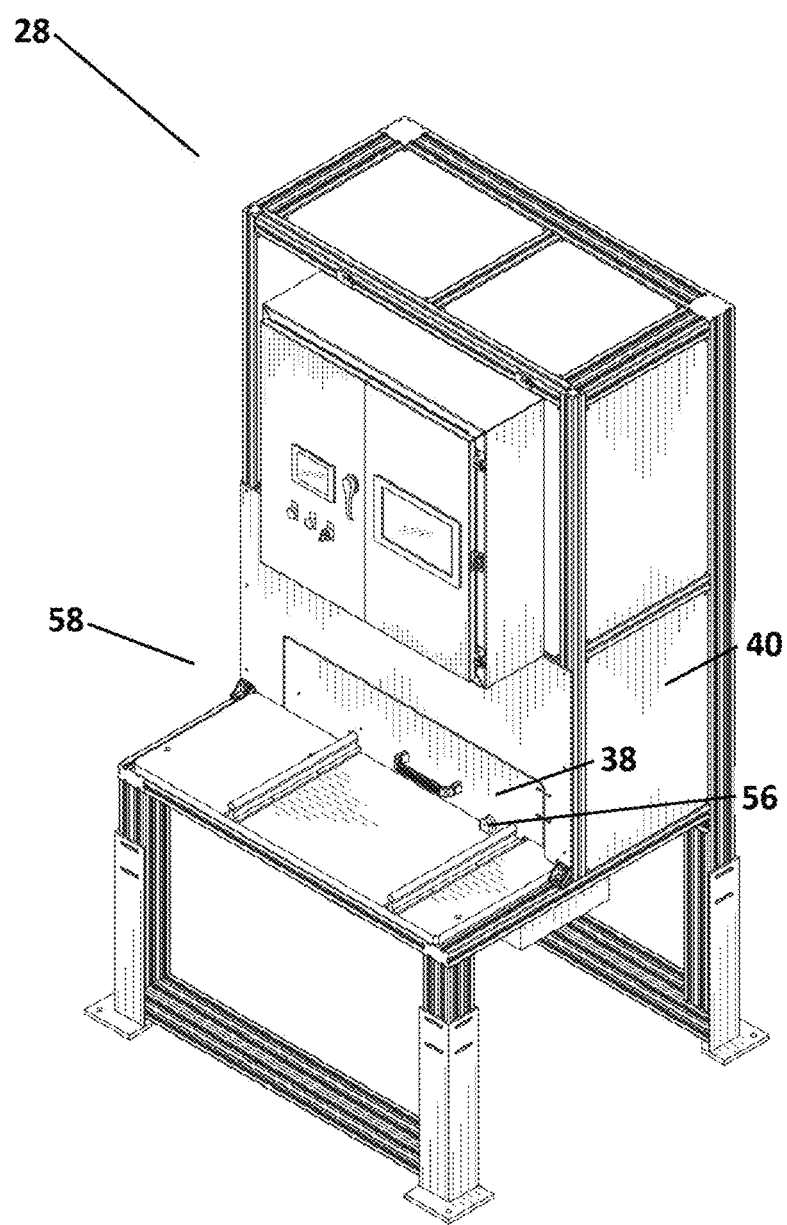
FIG. 9 illustrates a perspective view of the inspection apparatus with a machined metal component loaded for inspection and the apparatus in the inner inspection position in accordance with one embodiment.
Figure 10:
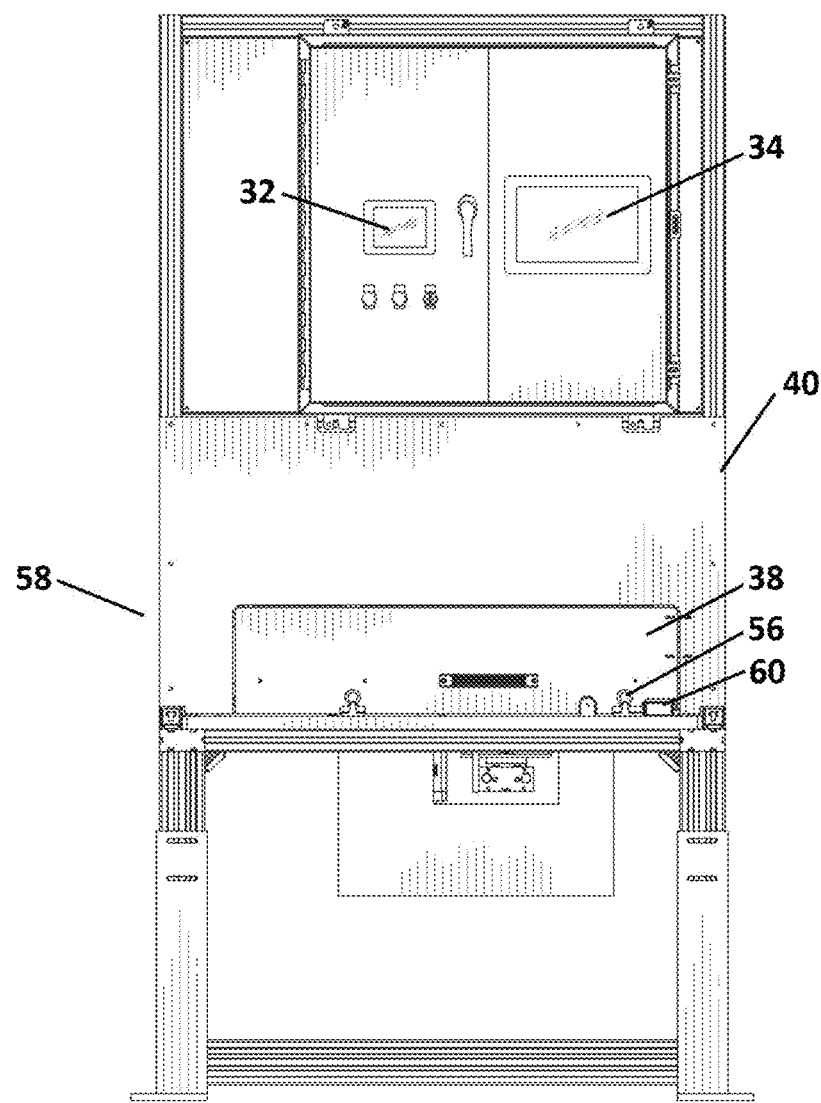
FIG. 10 illustrates a front view of the inspection apparatus with a machined metal component loaded for inspection and the apparatus in the inner inspection position in accordance with one embodiment.

Referring to FIG. 9 and FIG. 10, once the machined metal component 10 is loaded into the drawer 38, the drawer 38 is configured for movement from the outer loading position 36 (as seen in FIG. 7 and FIG. 8) to the inner inspection position 58. In the inner inspection position 58, the drawer 38, with the machined metal component 10 received and retained therein, is inside of the inner chamber 30 of the housing 40. In the embodiment of FIG. 9 and FIG. 10, the apparatus 28 may further comprise a sensor mechanism 56. The sensor mechanism 56 detects when the drawer 38 is in the inner inspection position 58. Once in the inner inspection position 58, the sensor mechanism 56 is operably connected to the controller mechanism 32 such that the sensor mechanism 56 signals to the controller mechanism 32 to permit automatic activation of the heating means 70 and the positioning means 68, in order to begin the inspection process.

Referring to FIG. 10, the apparatus 28 may further comprise locking means 60 for selectively locking and unlocking the drawer 38 within the inner chamber 30 when the drawer 38 is in the inner inspection position 58. The locking means 60 can comprise any locking means known in the art, such as bolt-lock system. Additionally, the locking means 60 may comprise a pneumatically activated bolt-lock system, which bolt-lock system can be automatically locked and unlocked by the controller mechanism 32 before and after the completion of the inspection process respectively. This controller mechanism 32 activated/de-activated locking prevents a user from moving the drawer 38 from the inner inspection position 58 to the outer loading position 36 prior to completion of the inspection process, thereby preventing user error and/or injury to a user.

FIG. 11 illustrates the apparatus 28 with outer wall 52 of the housing 40 removed along with the control shelf 46. As seen in the exemplary embodiment of FIG. 11, the inner chamber 30 may contain the IR detection device 66, the positioning means 68 and the heating means 70. From a practical perspective, this allows the operation of the apparatus 28 to take place entirely within the inner chamber 30 of the housing 40, in order to mitigate against user injuries and/or user error.

The drawer 38 may slide along a drawer frame railing 64 in order to move from the outer loading position 36 to the inner inspection position 58.

In the exemplary embodiment of FIG. 11, the IR detection device 66 is positioned above the machined metal component 10 and the drawer 38 and aimed downward towards the machined metal component 10 during the inspection process. A skilled artisan would appreciate that the IR detection device 66 can be positioned anywhere sufficient to allow the IR detection device 66 to detect an IR radiation signal emitted from the machined metal component 10. Positioning of the IR detection device 66 will depend on a number of factors, including without limitation the capabilities of the specific IR detection device 66 implemented, the ability to acquire an unobstructed view of the machined metal component 10 and the amount of precision required in capturing an adequate IR radiation signal, factors which are well within the purview and control of a skilled artisan.

Similarly, the heating means 70 and the positioning means 68 are positioned above the machined metal component 10 and the drawer 38 when the drawer 38 is in the inner inspection position 58. It would be within the capability of a skilled artisan to position the heating means 70 and the positioning means 68 as required in order to optimize the necessary application of heat in a variety of specific circumstances and the scope of the disclosed method and apparatus should not be limited to the exemplary positioning. The heating means 70 and the positioning means 68 can be secured in position to the housing 40 using any means known in the art, such as the mounting bar 62 used in the embodiment of FIG. 11.

Figure 12:
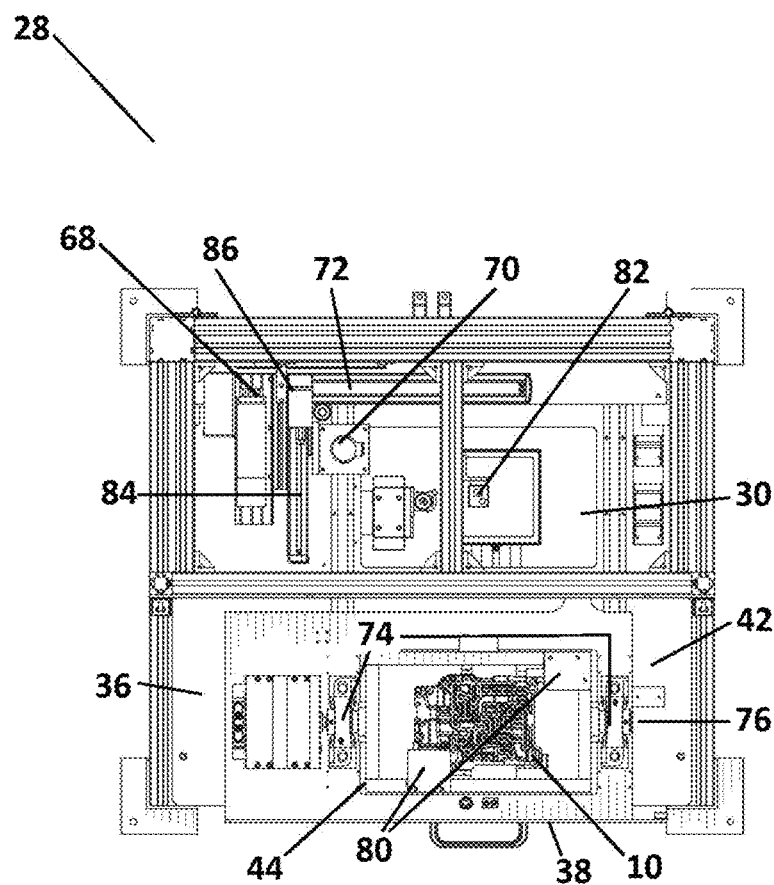
FIG. 12 illustrates a top view of the inspection apparatus with the apparatus in the outer loading position in accordance with one embodiment.

Referring to FIG. 12, a user may load the machined metal component 10 into the drawer 38 for inspection when the drawer 38 is in the outer loading position 36. The drawer 38 of the embodiment of FIG. 12 comprises a drawer frame 44, which drawer frame 44 is a fixture configured to receive and retain the machined metal component 10. The drawer frame 44 may further comprise a pair of drawer frame securing tabs 80, which tabs can be manually shifted into place by a user for further secure the machined metal component 10 within the drawer frame 44. Alternatively, the drawer frame securing tabs 80 may comprise hydraulic tabs that can be controlled by the controller mechanism 32 in order to automatically shift the drawer frame securing tabs 80 into position upon placing the machined metal component 10 within the drawer frame 44. This mechanism has the added benefit of ensuring that the machined metal component 10 is correctly placed into the drawer frame 44, given that the controller mechanism 32 can be configured to activate the drawer frame securing tabs 80 when the machined metal component 10 is correctly positioned within the drawer frame 44. Furthermore, this can also prevent the machined metal component 10 from being released from the drawer frame 44 until completion of inspection, as the controller mechanism 32 can be configured to release the drawer frame securing tabs 80 only upon completion of an inspection cycle.

The apparatus 28 may also comprise a component movement mechanism 42, the component movement mechanism 42 allowing for selective displacement of the of the machined metal component 10 relative to the heating means 70 to allow for heating of various sections of the machined metal component 10. The component movement mechanism 42 could comprise any number of mechanisms known in the art, including automated movement mechanisms such as servo-actuated or hydraulic actuated movers.

In the exemplary embodiment of FIG. 12, the component movement mechanism 42 comprises a rotational mechanism 76, which rotational mechanism 76 rotates the machined metal component 10 relative to the heating means 70. The rotational mechanism 76 may comprise one or more pneumatic cylinders, and the rotational mechanism 76 of the embodiment of FIG. 12 comprises a pair of pneumatic cylinders 74 positioned on each side of and connected to the drawer frame 44. The pneumatic cylinders 74 may be controlled by the controller mechanism 32, such that during the inspection cycle, the controller mechanism 32 may automatically cause the pneumatic cylinders 74 to rotate the drawer frame 44 to allow the heating means 70 to apply heat to various sections around the machined metal component 10, and thereafter allowing the IR detection device 66 to detect IR signals from each of the respective sections following heating.

Figure 13:
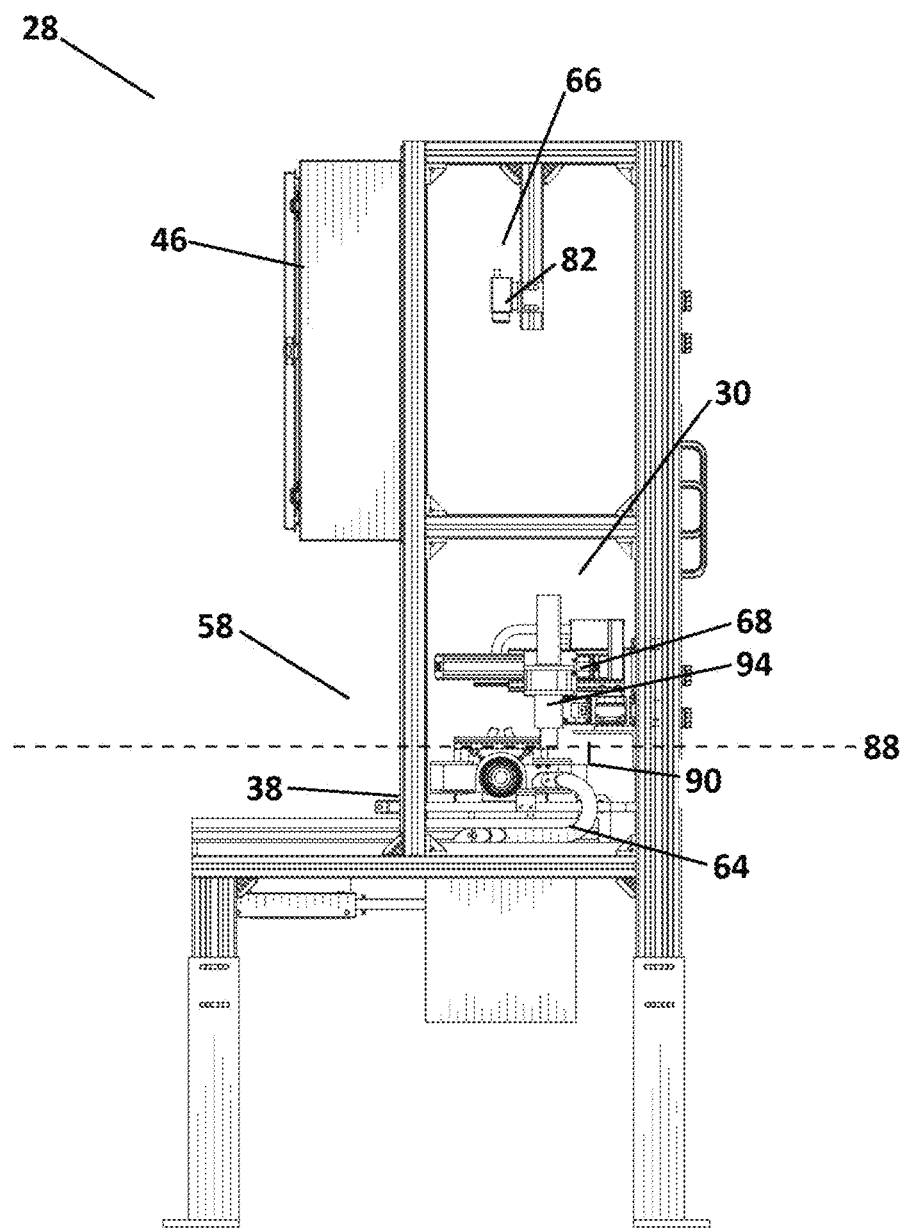
FIG. 13 illustrates a side view of the inspection apparatus with outer wall removed and the apparatus in the inner inspection position in accordance with one embodiment.

Referring to the illustration of FIG. 13, the IR detection device 66 of the exemplary embodiment comprises an IR camera 82. The IR camera 82 of the exemplary embodiment of FIG. 13 comprises any standard IR camera, such as those manufactured by FLIR A65 Camera with 25 mm lens and 640×512 pixel output. In the embodiment of FIG. 13, the IR camera 82 is positioned approximately 4 feet above the machined metal component 10 when the machined metal component 10 is in the inner inspection position 58. Based on the specific capabilities of the IR camera utilized, a skilled artisan could position the IR camera 82 at any position that would allow the IR camera 82 to adequately capture an IR radiation signal from the machined metal component 10 following heating.

The heating means 70 of the exemplary embodiment of FIG. 13 comprises a heat gun 94. In the exemplary embodiment of FIG. 13, the heat gun 94 comprises a standard hot air gun capable of producing pulses of hot air. The heat gun 94 implemented in the exemplary embodiment of FIG. 13 is a standard Steinel HG 2000E. The heat gun 94 can be mounted to the positioning means 68 using any standard mounting mechanism known in the art, such as a basic mounting bracket. A skilled artisan could use any number of available heating means 70 known in the art capable of creating a greater temperature elevation rate in one or more machined substrate fragments located in the one or more internal chambers 12 of the machined metal component 10 compared to the component temperature elevation rate. This could include any number of heat guns currently available, radiation heating elements as well as other IR heaters or other heating means in combination with air blowing means to circulate heat through the one or more internal chambers 12.

In the exemplary embodiment of FIG. 13, the positioning means 68 move the heating means 70 within a single plane 88 located at a predetermined height 90 relative to the outer surface 14 of the machined metal component 10. In the exemplary embodiment illustrated in FIG. 13, the predetermined height 90 of the single plane 88 is approximately 1.5 inches from the outer surface 14 of the machined metal component 10. A skilled artisan can position the heating means 70 at any predetermined location necessary, depending on the power of the heating means 70, the intricacy of the internal chambers of the machined metal component 10 and the detection requirements. Such modifications would be within the purview of a skilled artisan and the scope of the method and apparatus disclosed herein should not be limited to the positioning of the exemplary embodiment.

Figure 14:
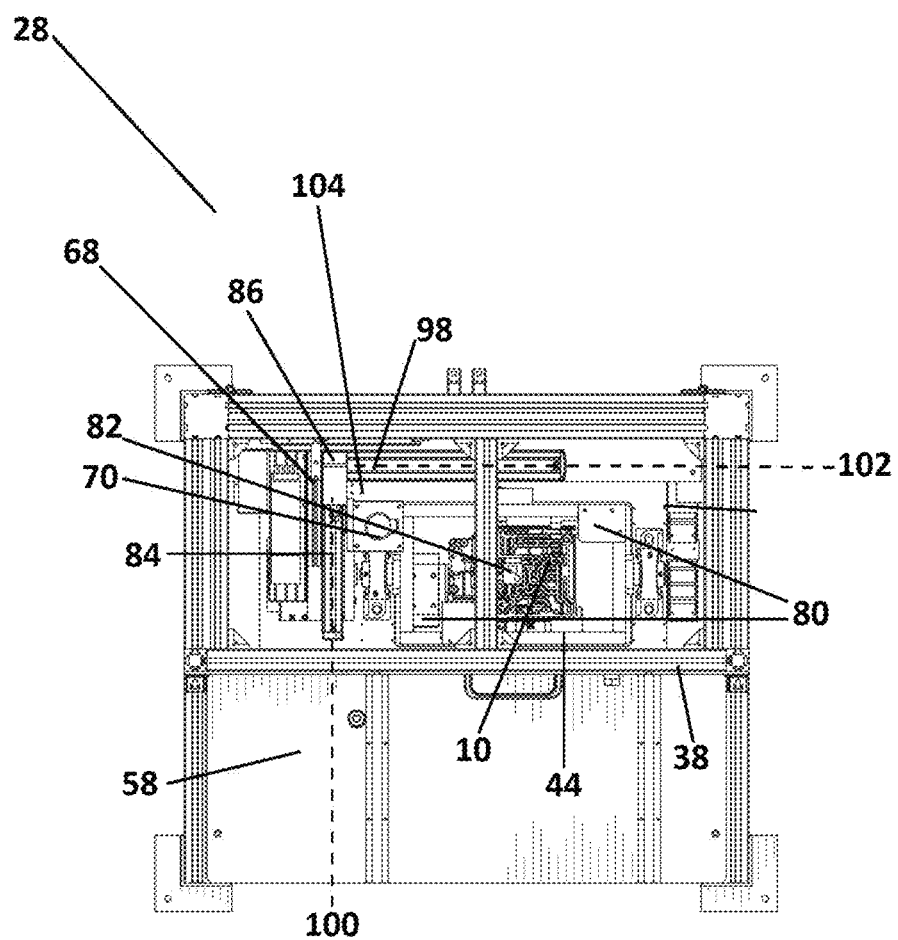
FIG. 14 illustrates a top view of the inspection apparatus with the apparatus in the inner inspection position in accordance with one embodiment.

FIG. 14 provides an overhead view of the exemplary embodiment, with the machined metal component 10 in the inner inspection position 58. As seen in FIG. 14, the IR camera 82 is positioned above the machined metal component 10 in order to capture a thermal image of the outer surface 14 of the machined metal component 10 following the application of heat by the heating means 70. The machined metal component 10 is held in place in the drawer 38 by the drawer frame securing tabs 80 in order prevent movement of the machined metal component 10 during the inspection process.

As seen in FIG. 14, the heating means 70 is mounted to a positioning means 68, which positioning means 68 move the heating means 70 to various locations relative to the outer surface 14 of the machined metal component 10. One skilled in the art could readily implement any number of positioning means 68 well known in the art, including without limitation such mechanisms as multi-axis robots, one or more servo-actuated linear sliders or any form of manually operated sliders. Accordingly, the scope of the positioning means 68 would include any means that can move the heating means 70 to various locations relative to the outer surface 14 of the machined metal component 10 and should not be limited in scope to the specific means of the exemplary embodiment.

In the exemplary embodiment of FIG. 14, the positioning means 68 comprises servo-actuated linear sliders 86. The heat gun 94 is mounted to the servo-actuated linear sliders 86 for movement relative to the outer surface 14 of the machined metal component 10. Specifically, in the exemplary embodiment of FIG. 14, the servo-actuated linear sliders 86 comprise a Y-axis linear slider 84 and an X-axis linear slider 98, which Y-axis linear slider 84 moves the heating means 70 along a Y-axis 100 within the single plane 88 (as illustrated in FIG. 13) and which X-axis linear slider 98 moves the heating means 70 along an X-axis 102 within the single plane 88 (as illustrated FIG. 13). In the illustrated exemplary embodiment of FIG. 14, the X-axis linear slider 72 and Y-axis linear slider 84 comprise standard servo-actuated linear sliders such as those produced by IAI. Also, the heating means 70 could be mounted to a multi-axis robot for movement in any number of directions.

The controller mechanism 32, which in the exemplary embodiment comprises a programmable logic controller, is operably connected to the servo-actuated linear sliders 86, to allow a user to program automatic movement of the heating means 70 to a plurality of different positions along the Y-axis 100 and the X-axis 102 within the single plane 88, to permit the Heating means 70 to apply heat to a plurality of locations defined on the outer surface of the machined metal component 10.

FIG. 14 illustrates the heating means 70 in a rest position 104. When in the rest position 104, the heating means 70 is positioned outside of the direct view of the IR camera 82, thereby providing the IR camera 82 with an unobstructed view of the outer surface 14 of the machined metal component 10.

Figure 15:
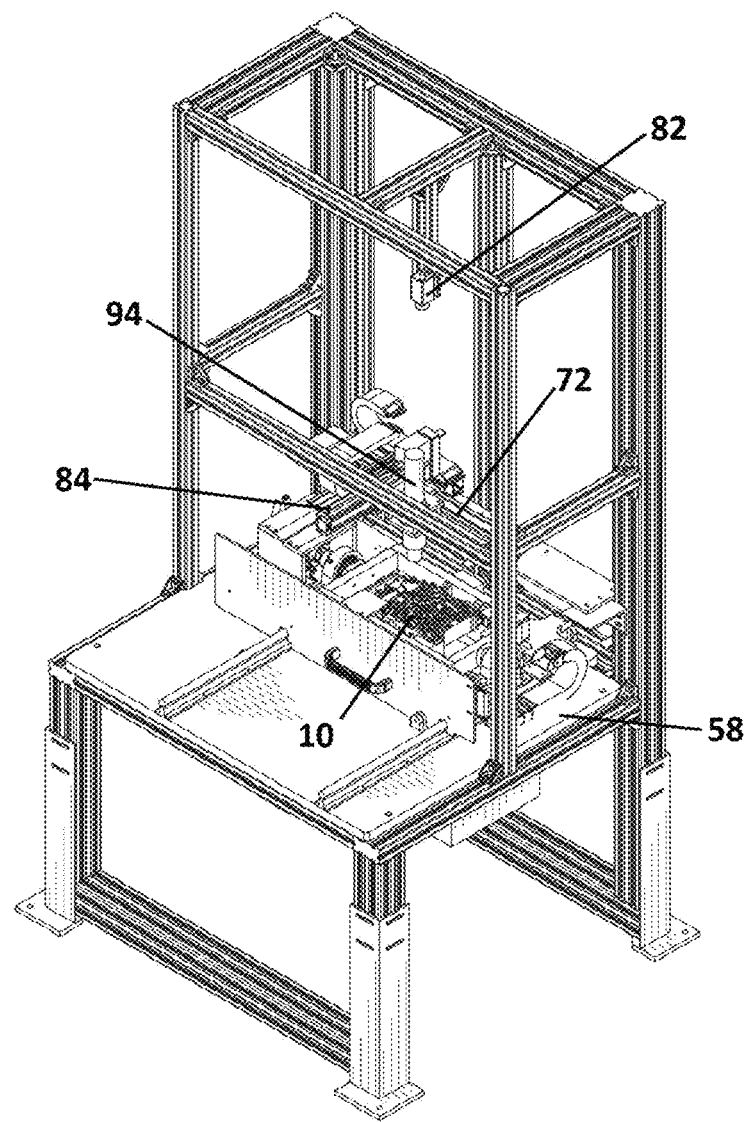
FIG. 15 illustrates a perspective view of the inspection apparatus with outer wall removed and the apparatus in the inner inspection position during inspection in accordance with one embodiment of the apparatus and method.
Figure 16:
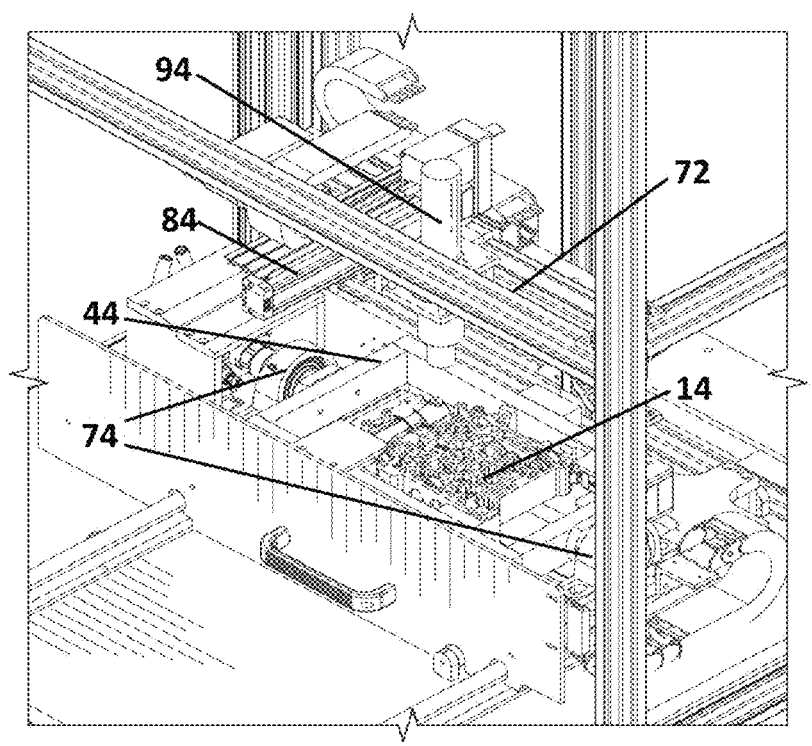
FIG. 16 illustrates an enlarged view of the apparatus and method of FIG. 15.

FIGS. 11 to 16 illustrate the functioning of the embodiment of apparatus 28 in accordance with the method disclosed herein. Referring to FIG. 4, FIG. 15 and FIG. 16, after the machined metal component 10 is loaded into inner inspection position 58, the controller mechanism 32 causes the X-axis linear slider 72 and Y-axis linear slider 84 to move the heat gun 94 from the rest position 104 to a position in the single plane 88 immediately above position I on the outer surface 14. Once reaching position I, the controller mechanism 32 will cause the heat gun 94 to apply a pulse of hot air at a temperature of 600 degrees Celsius for a duration of three (3) seconds to position I on the outer surface 14.

Following completion of the three (3) second duration of hot air pulse at position I, the controller mechanism 32 can cause the heat gun 94 to move along the X-axis linear slider 72 and Y-axis linear slider 84 back to the rest position 104. The heat gun 94 will remain at the rest position 104 for sufficient time to allow the IR camera 82 to capture the IR signal from the outer surface 14, which in the exemplary embodiment is approximately two (2) seconds. While at the rest position 104, the IR camera 82 will have unobstructed view of the outer surface 14 following the application of heat to position I, and can detect an IR radiation signal emitted from the outer surface 14 following the application of heat.

Figure 17:
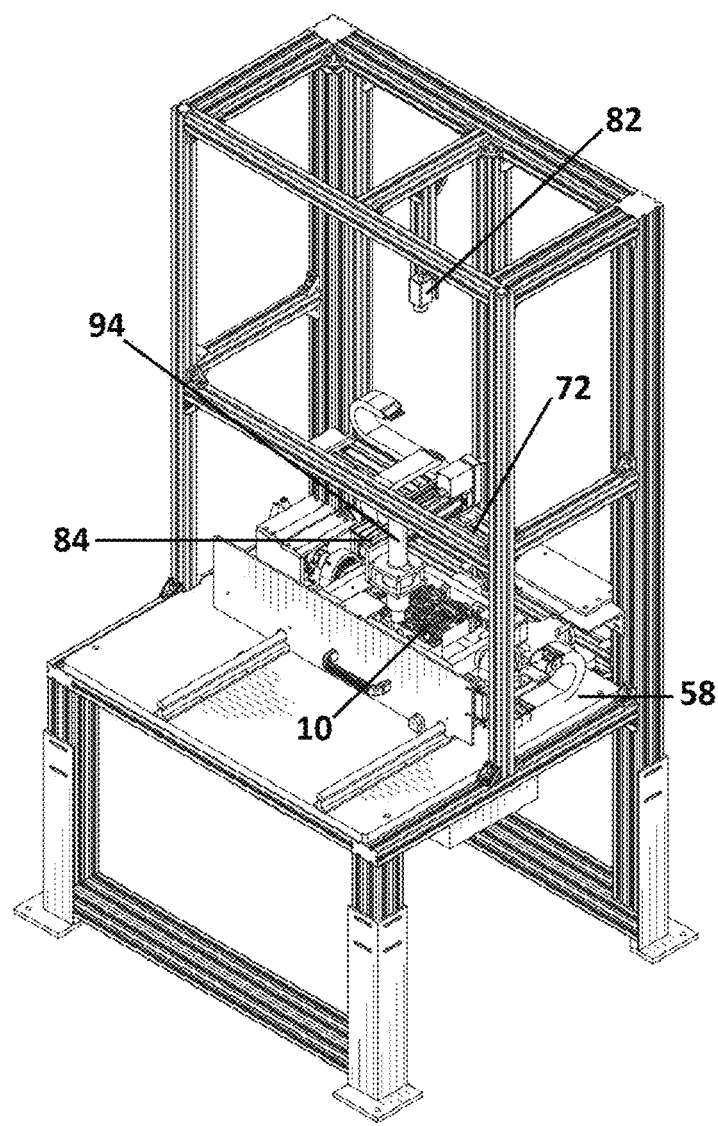
FIG. 17 illustrates a perspective view of the inspection apparatus with outer wall removed and the apparatus in the inner inspection position during inspection in accordance with one embodiment of the apparatus and method.
Figure 18:
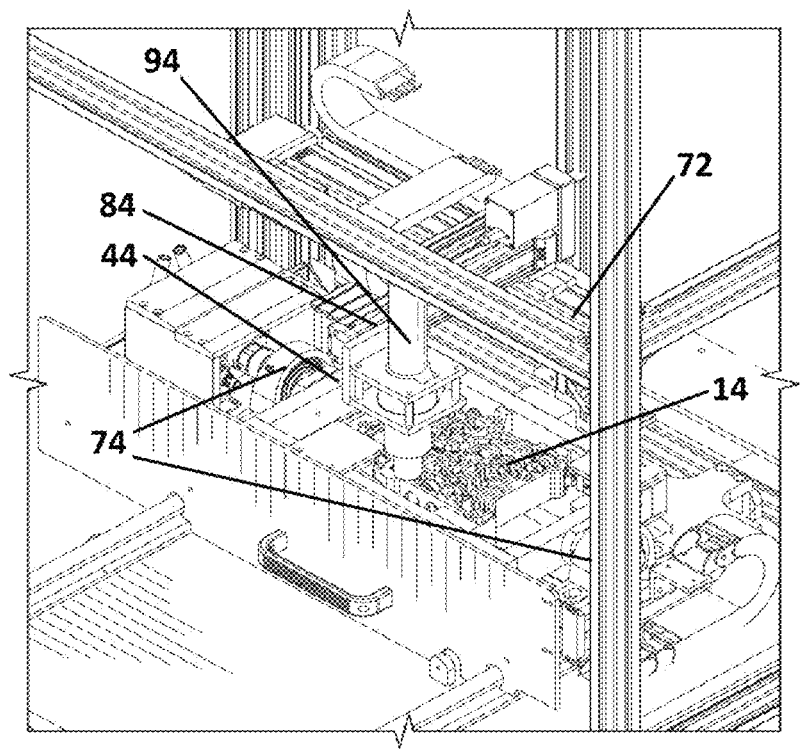
FIG. 18 illustrates an enlarged view of the apparatus and method of FIG. 17.
Figure 19:
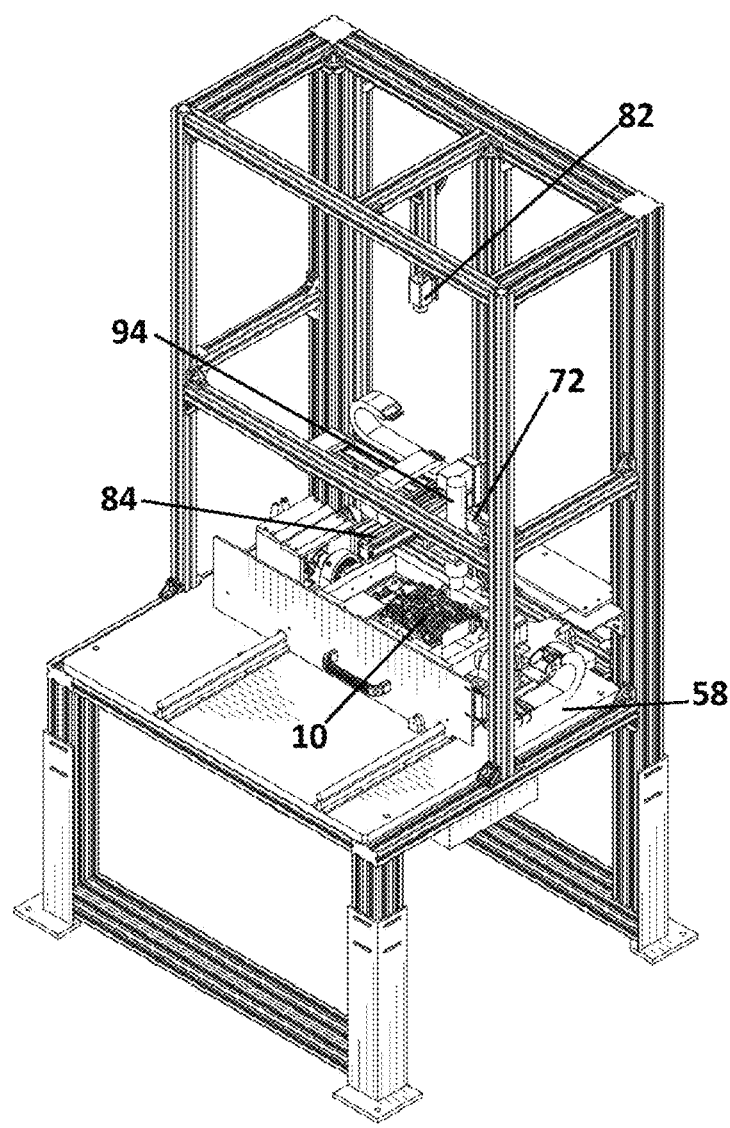
FIG. 19 illustrates a perspective view of the inspection apparatus with outer wall removed and the apparatus in the inner inspection position during inspection in accordance with one embodiment of the apparatus and method.

Referring to FIG. 4, FIG. 17 and FIG. 18, after completion of heating and IR radiation signal detection at the first position I, the controller mechanism 32 causes the X-axis linear slider 72 and Y-axis linear slider 84 to move the heat gun 94 from the rest position 104 to a position in the single plane 88 immediately above position II on the component surface 108. Once reaching position II, the controller mechanism 32 will cause the heat gun 94 to apply a pulse of hot air at a temperature of 600 degrees Celsius for a duration of five (5) seconds to position II.

Following completion of the five (5) second duration of hot air pulse at position II, the controller mechanism 32 can cause the heat gun 94 to move along the X-axis linear slider 72 and Y-axis linear slider 84 back to the rest position 104. The heat gun 94 will remain at the rest position 104 for approximately two (2) seconds. While at the rest position 104, the IR camera 82 will have unobstructed view of the outer surface 14 following the application of heat to position II, and can detect an IR radiation signal emitted from the outer surface 14 following the application of heat.

The controller mechanism 32 can cause automation of this cycle of consecutive movement of the heat gun 94 to each of the plurality of locations I-IX, causing the heat gun 94 to apply heat at each location for the requisite predetermined amount of time at each location and then returning to the rest position 104 to permit the IR camera 82 to detect an IR radiation signal emitted from the outer surface 14 following the application of heat. This process will proceed consecutively for each position I-IX, with the controller causing the heat gun 94 to move sequentially from each location to the next following the predetermined amount of time at each location.

As illustrated in FIG. 15 and FIG. 16, after moving through each position I-VIII, applying heat for the predetermined amount of time at each location I-VIII and detection of the IR radiation signal at each location I-VIII, the controller mechanism 32 moves the heat gun 94 to the final location IX. The controller mechanism 32 causes the heat gun 94 to apply a pulse of hot air for two (2) seconds to the final position IX. After completion of the two (2) second pulse of hot air, the controller mechanism 32 will cause the X-axis linear slider 72 and Y-axis linear slider 84 to move the heat gun 94 to the rest position 104 to permit the IR camera 82 to detect the IR radiation signal following the application of heat.

Figure 20:
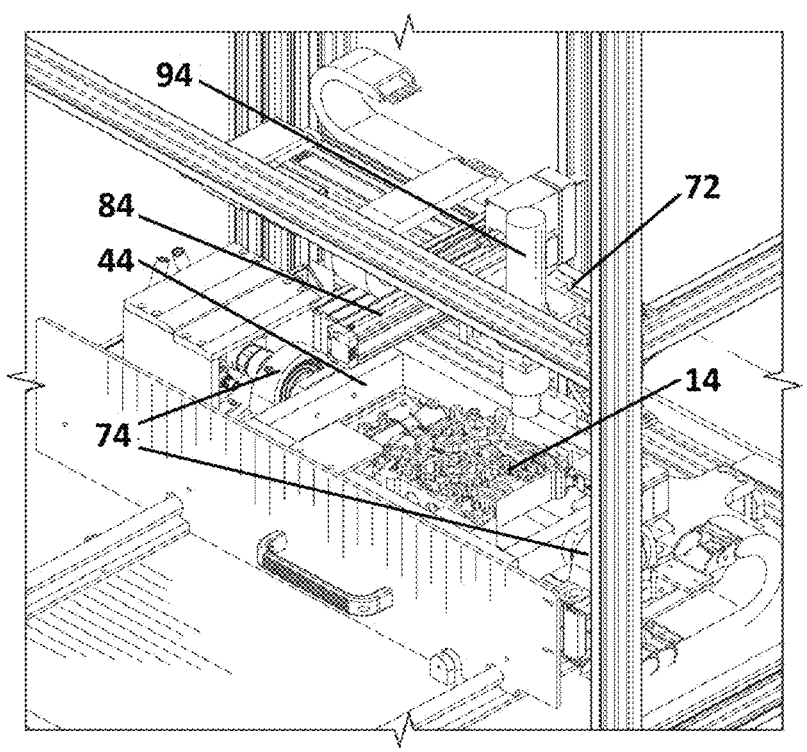
FIG. 20 illustrates an enlarged view of the apparatus and method of FIG. 19.

Optionally, the exemplary embodiment of FIGS. 11 to 16 may include a pair of pneumatic cylinders 74 connected to the drawer frame 44. The controller mechanism 32 can automatically cause the pneumatic cylinders 74 to rotate the drawer frame 44 and the machined metal component 10 to allow for the application of heat to other sections of the machined component body 22. In the embodiment of FIG. 20, following the application of heat at the final location IX and detection of the emitted IR radiation signal, the controller mechanism 32 may cause the pneumatic cylinders 74 to rotate the machined metal component 10 180 degrees to allow for the inspection method herein disclosed to similarly be applied to various locations on the opposing side (not illustrated) of the machined metal component 10.

Figure 21:
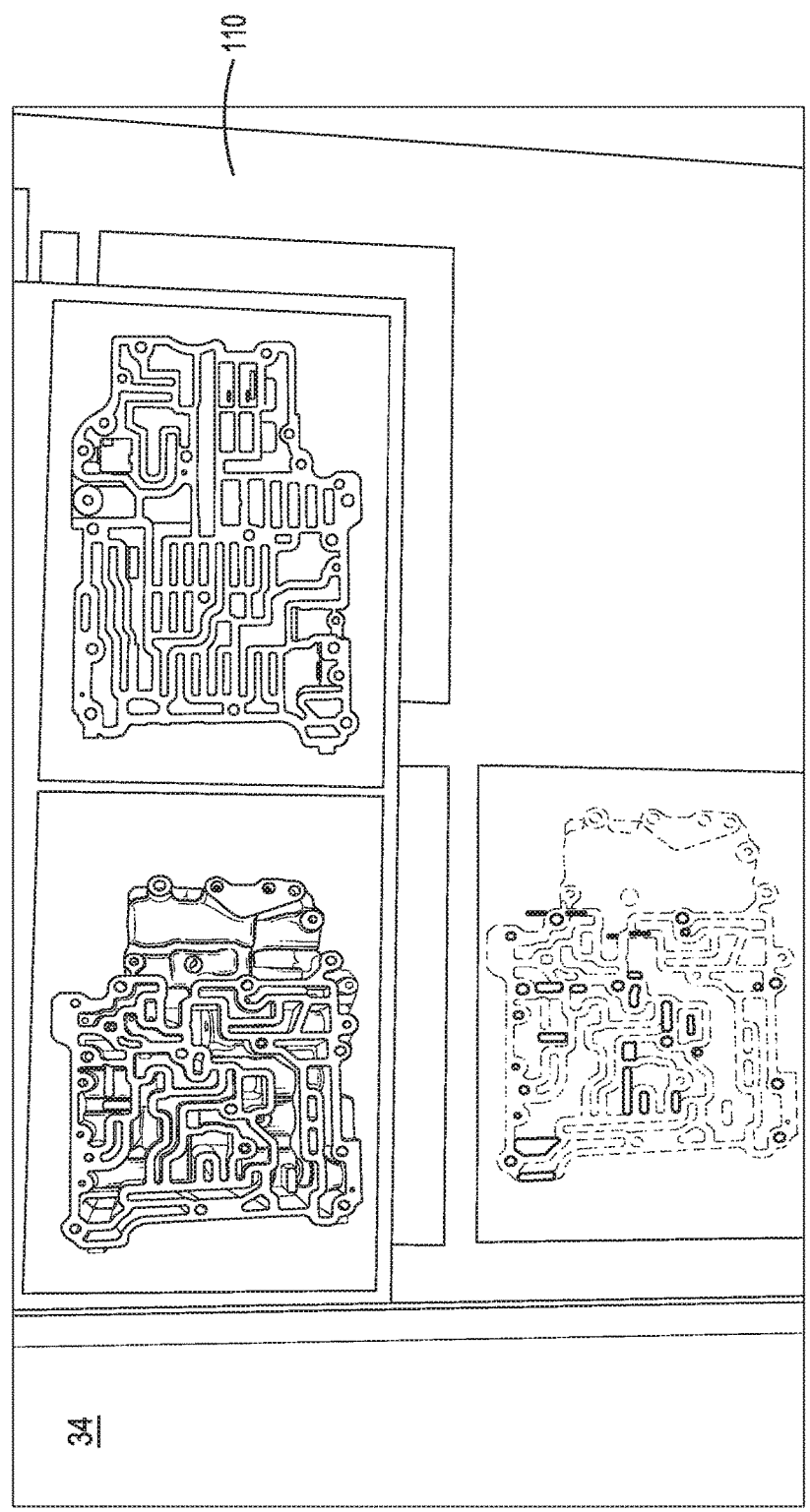
FIG. 21 is a picture of a visual output device in accordance with one embodiment.
Figure 22:
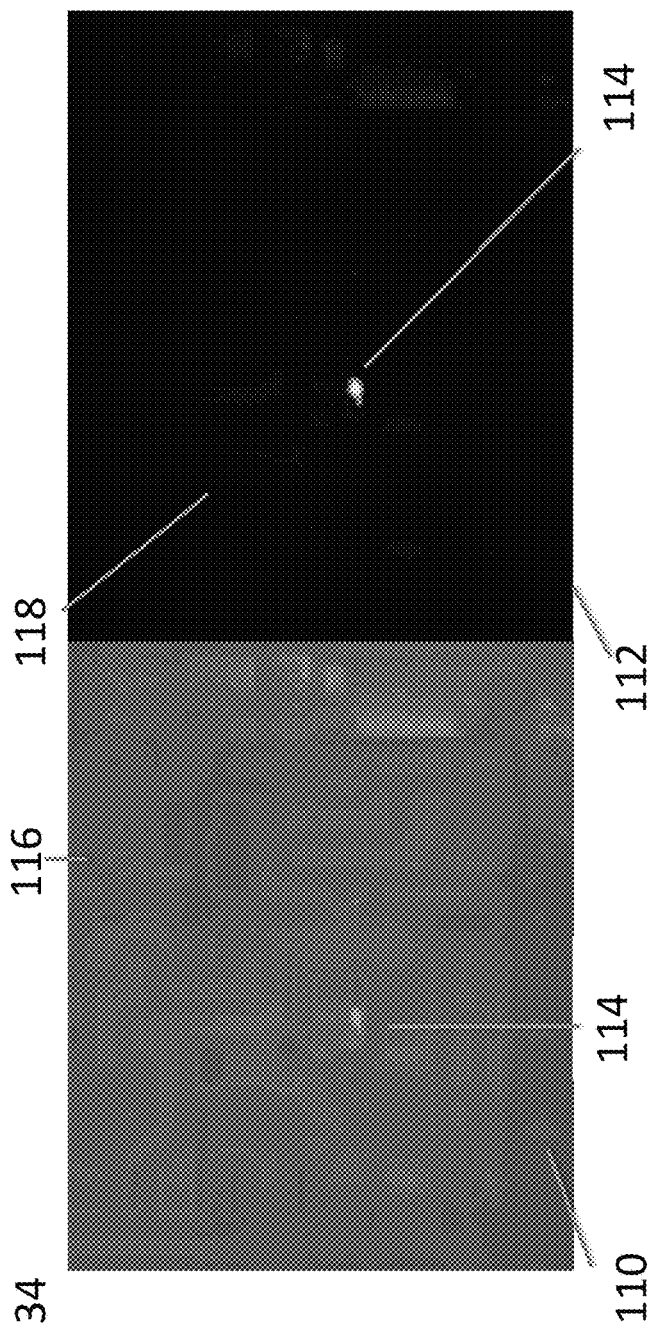
FIG. 22 is a picture of a visual output device displaying a thermal image of the machined metal component during inspection in accordance with one embodiment of the apparatus and method.

FIG. 21 and FIG. 22 illustrate the visual output device 34 of the exemplary embodiment, before and after the detection and outputting of the IR radiation signal in the thermal image 116 respectively. In the exemplary embodiment, at the first location I prior to the application of heat, the machined component body 22 and machined substrate fragment 24 both had temperature values of approximately 27 degrees Celsius, which was approximately equal to the temperature of the ambient surrounding environment. At the first position I, the heat gun 94 applied a sustained pulse of hot air for three (3) seconds in duration. Immediately thereafter, the machined substrate fragment 24 was approximately 112 degrees Celsius in temperature and the outer surface 14 was approximately 34 degrees Celsius in temperature. Given the large surface area, density, and weight of the machined component body 22, it is expected that there will be a relatively small component temperature elevation across the outer surface 14. However, given that the machined substrate fragment 24 is much smaller in size, with a surface area substantially surrounded by air within the one or more internal chambers 12, it is expected that the fragment temperature elevation rate will be greater than the component temperature elevation rate.

In the exemplary embodiment of FIG. 22, producing the thermal image 116 comprises directing the IR detection device 66 at the outer surface 14 of the machined metal component 10 to detect an IR radiation signal emitted from the outer surface 14, processing the IR radiation signal with a signal processor 54 operably connected to the IR detection device 66 and producing and outputting the thermal image 116 from the IR radiation signal on a visual output device 34 operatively connected to the signal processor 54. In the exemplary embodiment, heat is applied at each predetermined position I-IX for the predetermined amount of time. Following the application of heat at each position I-IX, the IR Camera 82 detects the IR radiation signal and the signal processor outputs a thermal image 116. This process of applying heat, detecting the IR radiation signal and outputting a thermal image occurs at each predetermined position I-IX.

Illustrated in FIG. 22 is the thermal image 116 created following application of heat at the fifth predetermined position V. Referring to FIG. 22, the IR camera 82 detected the IR radiation signal shortly after the completion of heating at the fifth location V, the signal processor 54 processed the IR radiation signal and outputted the thermal image 116 on the visual output device 34. The signal processor 54 of the exemplary embodiment of FIG. 22 is a standard Windows based PC operating standard image processing software. In this exemplary embodiment, the software used is VISIONPRO, produced by Cognex Corporation. The visual output device 34 can be a standard computer screen 110, and in the exemplary embodiment, the visual output device 34 is a standard touch screen HMI monitor.

The signal processor 54 is configured to process the IR radiation signal and output the IR radiation signal in the form of a color-temperature map 112 thermal image 116 on the computer screen 110. The color-temperature map 112 thermal image 116 may be configured to display colors corresponding with pre-defined temperatures across the thermal image 116 of the outer surface 14 of the machined metal component 10. In the exemplary embodiment of FIG. 22, given that the surrounding component temperature elevation 118 is approximately the same across the entire outer surface 14 (i.e. approximately 33 degrees Celsius) the majority of the thermal image 116 appears as a single color (the color black in FIG. 22) corresponding with approximately the same temperature across the outer surface 14. In contrast, the heat elevation points 114 appear as a different color from the surrounding areas of the outer surface 14 within the color-temperature map 112 thermal image 116. As illustrated in FIG. 22, the heat elevation points 114 appear as a shade of green. As the heat elevation points 114 appear as a different color, which color is configured to correspond with a specific temperature, in the exemplary embodiment of FIG. 22 the heat elevation points 114 indicate the presence of at least one machined substrate fragment 24 within one or more internal chambers 12 of the machined metal component 10.

Given that the fragment temperature elevation rate is greater than the component temperature elevation rate, the heat elevation points 114 comprise a positive temperature gradient between the heat elevation points 114 and the surrounding outer surface 14. This positive temperature gradient corresponds with the presence of a machined substrate fragment 24.

In the exemplary embodiment of FIG. 22, the IR camera 82 captures the IR radiation signal at a single point in time shortly after the completion of the heating process and the thermal image 116 is displayed as a color-temperature map 112 with specific colors corresponding with specific temperatures on the outer surface 14 at the point time when the IR radiation signal is captured. However, given that the machined substrate fragment 24 has a fragment temperature elevation rate that is greater than the component temperature elevation rate, in alternative embodiments the thermal image of temperature distribution may comprise a real-time transient image of temperature distribution across the outer surface 14.

In the exemplary embodiment of FIG. 22, immediately following the application of heat, the machined substrate fragment 24 was approximately 112 degrees Celsius in temperature and the machined component body 22 was approximately 34 degrees Celsius in temperature, indicating that the fragment temperature elevation rate was greater than the component temperature elevation rate. Therefore, a real-time transient image of temperature would also identify heat elevation points 114 corresponding with the presence of machined substrate fragments. Similarly, the fragment temperature cooling rate will also be greater than the component temperature cooling rate. In the exemplary embodiment of FIG. 22, the temperature of the machined substrate fragment 24 within approximately 6 seconds following the application of heat had declined from approximately 112 degrees Celsius to approximately 34 degrees Celsius. As such the thermal image 116 may be produced as a real-time transient image as the temperature of the outer surface 14 and the at least one machined substrate fragment 24 begins cooling to the temperature of the ambient surrounding environment following the heating step. Such modifications to the thermal image 116 can be carried out by a skilled artisan, and such a skilled person would be able to correlate heat elevation points 114 within the thermal image 116 to the presence of machined substrate fragment 24.

In accordance with the method herein described, the heat elevation points 114 comprise a positive temperature gradient between the heat elevation points 114 and the and the surrounding component temperature elevation 118. In accordance with the method herein described, the positive temperature gradient corresponds with the presence of a machined substrate fragment 24 within the one or more internal chambers 12 of the machined component body 22.

In some applications, one skilled in the art may wish to filter out heat elevation points 114 smaller than a predetermined minimum size or greater than a predetermined maximum size, as such heat elevation points 114 may constitute IR radiation signal noise, foreign material inclusions within the machined component body 22 that elevate in temperature at a greater rate than the surrounding outer surface 14, or other undesirable elements not requiring inspection.

In the exemplary embodiment of FIG. 22, machined substrate fragments 24 smaller than 2 millimeters×2 millimeters were considered negligible based on specifications of the exemplary embodiment. Fragments of such size can be correlated with a respective pixel size within the thermal image 116 of FIG. 22; in the exemplary embodiment, a 2 millimeters×2 millimeters fragment with correspond with a size of approximately 10-20 pixels within the thermal image 116. As such, the method may further comprise the steps of formatting the IR radiation signal with a low-pass size filter to remove heat elevation points smaller than a predetermined minimum size from the thermal image. In the exemplary embodiment, the low-pass size filter may remove heat elevation points 114 smaller than the corresponding pixel size within the thermal image 116, as such machined substrate fragments 24 would be negligible in size or such heat elevation points 114 may correspond with inclusions that do not constitute machined substrate fragments 24 within the one or more internal chambers 12. The method may optionally comprise the steps of formatting the signal with a high-pass size filter to remove heat elevation points larger than a predetermined maximum size from the thermal image.

As discussed above, in the exemplary embodiment of FIG. 22, the temperature difference value between the machined substrate fragment 24 and the outer surface 14 immediately following the application of heat is approximately 85-90 degrees Celsius. Foreign material inclusions in the machined component body 22 or other foreign materials may also absorb heat at different temperatures than the machined component body 22, thereby causing heat elevation points 114 to appear in the thermal image 116 which do not correspond with the presence of machined substrate fragments 24.

Knowing the approximate fragment temperature elevation rate and the standard difference in temperature value between the machined substrate fragment 24 and the outer surface 14 following the application of heat, a skilled artisan may optimize the processing of the thermal image to optionally include the steps of calculating at least one temperature difference value between the temperature of the at least one heat elevation points and the component temperature elevation. The signal processor may format the IR radiation signal with a low-pass temperature filter to remove heat elevation points corresponding with the temperature difference value being smaller than a predetermined minimum temperature difference value from the thermal image. As such, one skilled in the art may filter the thermal image 116 to remove heat elevation points 114 having temperatures that do not correspond with machined substrate fragments 24 resident within the one or more internal chambers 12. Similarly, one skilled in the art may optionally format the IR radiation signal with a high-pass temperature filter to remove heat elevation points corresponding with a temperature difference value being larger than a predetermined maximum temperature difference value from the thermal image.

The disclosed acts of optimizing the output format of the thermal image 116 and/or filtering the thermal image 116 can be deduced by the skilled artisan based upon the teachings contained within this disclosure. Through optimization, one skilled in the art can readily determine the appropriate temperature and duration for the application of heat in order to create the requisite fragment temperature elevation rate. Similarly, one skilled in the art can apply known color and filtering techniques in order to ensure that heat elevation points 114 appearing within the thermal image 116 correspond with machined substrate fragment 24 within the one or more internal chambers 12 of the machined component body 22. Such testing, IR radiation signal detection and image processing techniques can be deduced by the skilled artisan based upon the teachings contained within this disclosure.

The foregoing embodiments are described in an illustrative sense. Further features and sub-combinations of aspects of the disclosed method and apparatus will be evident to skilled artisans. All of these features and sub-combinations are intended to be encompassed by the following claims.

What is claimed is:

1. A method of inspecting a machined metal component in an ambient environment following a machining operation for detecting machined substrate fragments resident in the at least one internal chamber in a machined metal component, wherein the machined metal component includes a component body, the component body having an outer surface, and an interior region, the interior region having at least one internal chamber, the method comprising the steps of:

a) providing a profile of the machined metal component that has been subjected to a least one machining operation wherein the at least one internal chamber defined in the metal component communicates with at least one aperture defined in the outer surface of the component body providing open exposure of the at least one internal chamber to the ambient surrounding environment;

b) identifying one or more points defined on the outer surface, the one or more points each corresponding with an aperture communicating with one or more internal chambers;

c) moving a heating element configured to deliver a pulse of hot air to the one or more points defined on the outer surface and applying a pulse of hot air sequentially to the one or more points defined on the outer surface for a time interval at each of the one or more points, wherein the pulse of hot air is applied to each of the one or more points defined on the outer surface sequentially following the expiration of the time interval at each location, the application of hot air sufficient in temperature and duration to cause a fragment temperature elevation in at least one machined substrate fragment separated from the component body during the machining operation present in the at least one internal chamber following the machining operation, and a component temperature elevation in the machined metal component, wherein the fragment temperature elevation has a fragment temperature elevation rate and the component temperature elevation has a component temperature elevation rate and wherein the fragment temperature elevation rate is greater than the component temperature elevation rate, wherein the at least one machined substrate fragment is composed of the same material substance as the machined metal component and was removed from the machined metal component during the machining operation;

d) producing a thermal image of temperature distribution of the outer surface of the machined metal component following the application of heat the pulse of hot air for the time interval at each one of the one or more points;

e) detecting one or more heat elevation points within the thermal image of the temperature distribution of the outer surface, the heat elevation points indicating the presence of at least one machined substrate fragment resident within one or more internal chambers of the machined metal component following the machining operation.

2. The method of claim 1, wherein the profile is an open cross-sectional profile of the machined metal component.

3. The method of claim 1 further comprising the steps of:
moving the heating element to a rest position following the application of the pulse of hot air for the predetermined amount of time at each of the one or more points;
producing a thermal image of temperature distribution of the outer surface of the machined metal component while the heating element is in the rest position.

4. The method of claim 1, wherein the thermal image of temperature distribution is a real-time transient image, and wherein the thermal image is produced as the temperature of the outer surface and the at least one machined substrate fragment begins cooling to the temperature of the ambient surrounding environment following the heating step.

5. The method of claim 1, wherein the step of producing the thermal image comprises directing an IR detection device at the outer surface of the machined metal component to detect an IR radiation signal emitted from the outer surface, processing the IR radiation signal with a signal processor operably connected to the IR detection device and producing and outputting the thermal image from the IR radiation signal on a visual output device operatively connected to the signal processor.

6. The method of claim 5, wherein the step of processing the IR radiation signal with a signal processor further comprises formatting the signal with a low-pass size filter to remove heat elevation points smaller than a predetermined minimum size from the thermal image.

7. The method of claim 6, wherein the predetermined minimum size is five pixels.

8. The method of claim 5, wherein the step of processing the IR radiation signal with a signal processor further comprises formatting the signal with a high-pass size filter to remove heat elevation points larger than a predetermined maximum size from the thermal image.

9. The method of claim 5, further comprising calculating at least one temperature difference value between the temperature of the at least one heat elevation points and the component temperature elevation and wherein processing the IR radiation signal with a signal processor further comprises formatting the signal with a low-pass temperature filter to remove heat elevation points corresponding with the temperature difference value being smaller than a predetermined minimum temperature difference value from the thermal image.

10. The method of claim 5, further comprising calculating at least one temperature difference value between the temperature of the at least one heat elevation points and the component temperature elevation, and wherein processing the IR radiation signal with a signal processor further comprises formatting the signal with a high-pass temperature filter to remove heat elevation points corresponding with the temperature difference value being larger than a predetermined maximum temperature difference value from the thermal image.

11. The method of claim 5, wherein the signal processor is a computer and the output device is a computer screen operably connected to the computer, wherein the computer is configured to process the IR radiation signal and output the IR radiation signal in the form of a color-temperature map thermal image on the computer screen.

12. The method of claim 11 wherein the color-temperature map thermal image is configured to display colors corresponding with pre-defined temperatures across the thermal image of the outer surface of the machined metal component.

13. The method of claim 12, wherein the heat elevation points appear as a different color from surrounding areas of the outer surface within the color-temperature map thermal image.

14. The method of claim 1, wherein the machined metal component comprises a metal or a metallic alloy.

15. The method of claim 1, wherein the machined substrate fragment is substantially surrounded by ambient air within the internal chamber.

16. The method of claim 15, wherein the machined substrate fragment is a metallic chip separated from the machined component body during the machining process.

17. The method of claim 1, wherein the heat elevation points comprise a positive temperature gradient between the heat elevation points and the surrounding outer surface.

18. The method of claim 17, wherein the positive temperature gradient corresponds with the presence of a machined substrate fragment.

19. An apparatus for inspecting a machined metal component following a machining operation, the machined metal component comprising a component body having at least one internal chamber, the internal chamber communicating with at least one aperture defined on an outer surface of the component body, comprising:
   a) heating element configured to apply a pulse of hot air to at least one section of an outer surface of the machined metal component;
   b) a positioning element configured to move the heating element along one or more axes to one or more points relative to the at least one section of the outer surface, wherein the at least one section of the outer surface correspond to the at least one aperture communicating with the internal chamber;
   c) a controller mechanism, the controller mechanism operably connected to the positioning element and the heating element to permit selective control of the application of the pulse of hot air to the aperture defined on the outer surface and the positioning of the heating element relative to the aperture defined in the outer surface;
   d) a thermal detection device, wherein the thermal detection device is an infrared (IR) detector and is positioned to detect an IR radiation signal emitted from the at least one section of the outer surface;
   e) a signal processor, operably connected to the thermal detection device to receive and process the detected IR radiation signal; and
   f) a visual output device operatively connected to the signal processor for receiving the processed IR radiation signal and displaying a thermal image of the IR radiation signal emitted from the section of the outer surface.

20. The apparatus of claim 19 further comprising a housing having an outer wall defining an inner chamber, the inner chamber containing the IR detection device, the positioning means and the heating element.

21. The apparatus of claim 20, wherein the housing comprises a drawer configured to receive and retain the machined metal component, the drawer configured for movement from an outer loading position, wherein at least a portion of the drawer is outside of the inner chamber to allow loading of the machined metal component, and an inner inspection position, wherein the drawer is inside of the inner chamber.

22. The apparatus of claim 21, wherein the drawer comprises locking means for selectively locking and unlocking the drawer within the inner chamber when the drawer is in the inner inspection position.

23. The apparatus of claim 21 further comprising a sensor mechanism, the sensor mechanism configured to detect when the drawer is in the inner inspection position and operably connected to the controller mechanism to permit activation of the heating means and positioning means when the drawer is in the inner inspection position.

24. The apparatus of claim 19, wherein the positioning means move the heating means within a single plane located at a predetermined height relative to the outer surface.

25. The apparatus of claim 19, wherein the positioning means comprises one or more servo-actuated linear sliders, the heating means being mounted to the one or more servo-actuated linear sliders for movement.

26. The apparatus of claim 25, wherein the one or more servo-actuated linear sliders comprise an X-axis linear slider for moving the heating means within an X-axis within a single plane and a Y-axis linear slider for moving the heating means within a Y-axis within a single plane.

27. The apparatus of claim 25, further comprising a component movement mechanism, the component movement mechanism allowing for selective displacement of the machined metal component relative to the heating means to allow for heating of various sections of the machined component.

28. The apparatus of claim 27, wherein the component movement mechanism comprises a rotational mechanism, the rotational mechanism rotating the machined metal component relative to the heating means.

29. The apparatus of claim 28, wherein the rotational mechanism comprises one or more pneumatic cylinders, the pneumatic cylinders being releasably securable to the machined metal component.

30. A method of inspecting a machined metal component in a surrounding ambient environment, the machined metal component defining a component body, the component body having an outer surface, and an interior region, the interior region having at least one internal chamber, for detecting machined substrate fragments resident in the at least one internal chamber, the internal chamber communicating with at least one aperture defined on a surface of the machined metal component, the method comprising the steps of:

providing an apparatus for inspecting a machined component, the apparatus including:

a heating element configured to apply a pulse of hot air to at least a section of one aperture defined on the component surface of the machined metal component and communicating with the internal chamber;

a positioning element configured to move the heating element along one or more points of the heating element relative to the aperture defined on the outer surface;

a controller mechanism, the controller mechanism operably connected to the positioning means and heating means to permit selective control of the application of a pulse of hot air to the aperture defined in the outer surface and the positioning of the heating element relative to the outer surface;

an IR detection device, positioned to detect an IR radiation signal emitted from the section of the component surface;

a signal processor, operably connected to the IR detection device to receive and process the detected IR radiation signal; and a visual output device operatively connected to the signal processor for receiving the processed IR radiation signal and displaying a thermal image of the IR radiation signal emitted from the section of the component surface;

providing a profile of the machined component wherein the at least one internal chamber communicates with at least one aperture defined in the outer surface providing open exposure of the at least one internal chamber to the ambient surrounding environment;

identifying one or more points defined in the outer surface, the one or more points each corresponding with an aperture communicating with one or more internal chambers;

moving the heating element configured to deliver the pulse of hot air to the one or more points defined on the outer surface and applying a pulse of hot air sequentially to the one or more points defined on the outer surface for a time interval at each of the one or more points, wherein the pulse of hot air is applied to each of the one or more points defined on the outer surface sequentially following the expiration of the time interval for each location, the application of heat sufficient in temperature and duration to cause a fragment temperature elevation in at least one machined metal fragment present in the at least one internal chamber and a component temperature elevation in the machined metal component, wherein fragment temperature elevation has a fragment temperature elevation rate and the component temperature elevation has a component temperature elevation rate and wherein the fragment temperature elevation rate is greater than the component elevation rate;

producing a thermal image of temperature distribution of the component surface of the machined metal component following the application of the pulse of hot air for the predetermined amount of time at each of the one or more points, detecting one or more heat elevation points within the thermal image of the temperature distribution output of the component surface, the heat elevation points indicating the presence of at least one machined substrate fragment within one of the one or more internal chambers of the machined metal component.

* * * * *